US008350042B2

(12) United States Patent
Hermann et al.

(10) Patent No.: US 8,350,042 B2
(45) Date of Patent: Jan. 8, 2013

(54) ANTIVIRAL COMPOUNDS FOR THE TREATMENT OF HCV INFECTION

(75) Inventors: Thomas C. Hermann, Cardiff by the Sea, CA (US); Maia Carnevali, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 307 days.

(21) Appl. No.: 12/865,385

(22) PCT Filed: Jan. 29, 2009

(86) PCT No.: PCT/US2009/032476
§ 371 (c)(1),
(2), (4) Date: Aug. 6, 2010

(87) PCT Pub. No.: WO2009/099897
PCT Pub. Date: Aug. 13, 2009

(65) Prior Publication Data
US 2011/0003855 A1    Jan. 6, 2011

Related U.S. Application Data

(60) Provisional application No. 61/025,264, filed on Jan. 31, 2008.

(51) Int. Cl.
*C07D 211/56* (2006.01)
*C07D 489/00* (2006.01)
*A61K 31/535* (2006.01)
*A61M 5/00* (2006.01)

(52) U.S. Cl. ......... 546/223; 546/244; 514/329; 604/187

(58) Field of Classification Search ................... 546/223, 546/244; 514/329; 604/187
See application file for complete search history.

(56) References Cited

U.S. PATENT DOCUMENTS

| | | | |
|---|---|---|---|
| 6,750,348 B1 | 6/2004 | Bridger et al. | |
| 7,223,759 B2 | 5/2007 | Zhou et al. | |
| 2004/0235823 A1 | 11/2004 | Bridger et al. | |

FOREIGN PATENT DOCUMENTS

| | | |
|---|---|---|
| EP | 0250172 A2 | 12/1987 |
| WO | WO 00-56729 A1 | 9/2000 |
| WO | WO 2005-028467 A1 | 3/2005 |

OTHER PUBLICATIONS

International Search Report issued in corresponding PCT Application No. PCT/US2009/032476, mailed Jun. 29, 2009.
Auerbach et al, Antibiotics targeting ribosomes: crystallographic studies, Current Drug Targets—Infectious Disorders, 2002, vol. 2, pp. 169-186.
Ayida et al, Synthesis of dehydroalanine fragments as thiostrepton side chain mimetics, Bioorganic & Medicinal Chemistry Letters, 2005, vol. 15, pp. 2457-2460.
Banerjee et al, Specific interaction of hepatitis C virus protease/helicase NS3 with the 3'-terminal sequences of viral positive- and negative-strand RNA. Journal of Virology, Feb. 2001, vol. 75, No. 4, pp. 1708-1721.
Barluenga et al, Rational design of azepane-glycoside antibiotics targeting the bacterial ribosome. Bioorganic & Medicinal Chemistry Letters, 2004, vol. 14, pp. 713-718.
Bartenschlager et al, Novel cell culture systems for the hepatitis C virus, Antiviral Research, 2001 vol. 52, pp. 1-17.
Beales et al, The internal ribosome entry site (IRES) of hepatitis C virus visualized by electron microscopy, RNA Society, 2001, vol. 7, pp. 661-670.
Blight et al, Molecular virology of hepatitis C virus: an update with respect to potential antiviral targets, Antiviral Therapy, 1998, vol. 3, pp. 71-81.
Blount et al, Using pyrene-labeled HIV-1 TAR to measure RNA-small molecule binding, Nucleic Acids Research, 2003 vol. 31, No. 19, Oxford University Press.
Boehringer, et al, Structure of the Hepatitis C Virus IRES Bound to the Human 80S Ribosome: Remodeling of the HCV IRES, Structure, Nov. 2005, vol. 13, pp. 1695-1706.
Bradrick et al, Ligand-induced changes in 2-aminopurine fluorescence as a probe for small molecule binding to HIV-1 TAR RNA, RNA Society, 2004, vol. 10, pp. 1459-1468.
Brands et al, Novel antibiotics for the treatment of gram-positive bacterial infections, Journal of Medicinal Chemistry, 2002, vol. 45, pp. 4246-4253.
Brown et al, Secondary structure of the 5' nontranslated regions of hepatitis C virus and pestivirus genomic RNAs, Nucleic Acids Research, 1992, vol. 20, No. 19, pp. 5041-5045, Oxford Univ. Press.
Brunel et al, Probing RNA structure and RNA-ligand complexes with chemical probes, Methods in Enzymology, 2000, vol. 318, pp. 3-21.
Bustin, S. A., Absolute quantification of mRNA using real-time reverse transcription polymerase chain reaction assays, Journal of Molecular Endocrinology, 2000, vol. 25, pp. 169-193.
Cheng et al, Specific Interaction between the Hepatitis C Virus NS5B RNA Polymerase and the 3' End of the Viral RNA, Journal of Virology, Aug. 1999, vol. 73, No. 8, pp. 7044-7049.
Collier et al, A conserved RNA structure within the HCV IRES eIF3-binding site, Natural Structural Biology, vol. 9, No. 5, pp. 375-380, May 2002 (published online Apr. 1, 2002).
Collier, et al, Translation efficiencies of the 5' untranslated region from representatives of the six major genotypes of hepatitis C virus using a novel bicistronic reporter assay system, Journal of General Virology, vol. 79, pp. 2359-2366, 1998.
Cory, et al, Use of an Aqueous Soluble Tetrazolium/Formazan Assay for Cell Growth Assays in Culture, Cancer Communications, vol. 3, No. 7, pp. 207-212, Jul. 1991.

(Continued)

*Primary Examiner* — Janet Andres
*Assistant Examiner* — John Mabry
(74) *Attorney, Agent, or Firm* — Knobbe Martens Olson & Bear LLP

(57) ABSTRACT

Disclosed are compounds and methods of synthesis of Formula I for the development of antiviral drugs for the treatment of HCV infection.

38 Claims, 9 Drawing Sheets

OTHER PUBLICATIONS

Curry, Michael, Hepatitis B and hepatitis C viruses in liver transplantation, Transplantation, Oct. 15, 2004, vol. 78, No. 7, pp. 955-963.

De Francesco et al, Approaching a new era for hepatitis C virus therapy: inhibitors of the NS3-4A serine protease and the NS5B RNA-dependent RNA polymerase, Antiviral Research, 2003, vol. 58, pp. 1-16.

DeJong et al, Proflavine acts as a Rev inhibitor by targeting the high-affinity Rev binding site of the Rev responsive element of HIV-1, Biochemistry, 2003, vol. 42, pp. 8035-8046.

Dibrov et al, Functional Architecture of HCV IRES Domain II Stabilized by Divalent Metal Ions in the Crystal Metal Ions in the Crystal and in Solution, Angew. Chem. Int. Ed. 2007, vol. 46, pp. 226-229.

Domitrovich et al, Role of La autoantigen and polypyrimidine tract-binding protein in HCV replication, Virology, 2005, vol. 335, pp. 72-86.

Drysdale et al, RNA as a drug target, Progress in Medicinal Chemistry, 2002, vol. 39, pp. 73-119.

Dutkiewicz et al, Structural characterization of the highly conserved 98-base sequence at the 3' end of HCV RNA genome and the complementary sequence located at the 5' end of the replicative viral strand, Nucleic Acids Research, 2005, vol. 33, No. 2, pp. 693-703.

Fingl et al, The Pharmacological Basis of Therapeutics, Chapter 1: General Principles, MacMillan Publishing Co., Inc., 1975.

Fourmy et al, Structure of the A site of *Escherichia coli* 16S ribosomal RNA complexed with an aminoglycoside antibiotic, Science, Nov. 22, 1996, vol. 274, No. 5291, pp. 1367-1371.

Francois et al, Antibacterial aminoglycosides with a modified mode of binding to the ribosomal-RNA decoding site, Angew Chem Int Ed Engl, 2004, vol. 43, pp. 6735-6738.

Friebe et al, Genetic Analysis of Sequences in the 3' Nontranslated Region of Hepatitis C Virus That are Important for RNA Replication, Journal of Virology, Jun. 2002, vol. 76, No. 11, pp. 5326-5338.

Friebe et al, Kissing-Loop Interaction in the 3' End of the Hepatitis C Virus Genome Essential for RNA Replication, Journal of Virology, Jan. 2005, vol. 79, No. 1, pp. 380-392.

Friebe et al, Sequences in the 5' Nontranslated Region of Hepatitis C Virus Required for RNA Replication, Journal of Virology, Dec. 2002, vol. 75, No. 24, pp. 12047-12057.

Gallego et al, Targeting RNA with small-molecule drugs: therapeutic promise and chemical challenges, Acc Chem Res, 2001, vol. 34, pp. 836-843.

Gallego et al, The hepatitis C virus internal ribosome-entry site: a new target for antiviral research, Biochemical Society Transactions, 2002, vol. 30, part 2.

Han et al, Molecular recognition by glycoside pseudo base pairs and triples in an apramycin-RNA complex, Angew Chem Int Ed Engl, 2005, vol. 44, pp. 2694-2700.

Hawkins, Mary, Fluorescent pteridine nucleoside analogs: a window on DNA interactions, Cell Biochemistry and Biophysics, 2001, vol. 34, pp. 257-281.

Hermann et al, Aminoglycoside binding to the hammerhead ribozyme: a general model for the interaction of cationic antibiotics with RNA, J. Mol. Biol., 1998, vol. 276, pp. 903-912.

Hermann et al, Docking of cationic antibiotics to negatively charged pockets in RNA folds, J Med Chem, 1999, vol. 42, pp. 1250-1261.

Hermann et al, Rational drug design and high-throughput techniques for RNA targets, Comb Chem High Throughput Screen, 2000, vol. 3, pp. 219-234.

Hermann et al, RNA as a target for small-molecule therapeutics, Expert Opin Ther Patents, 2005, vol. 15, pp. 49-62.

Hermann et al, Saccharide-RNA recognition, Biopolymers (Nucleic Acid Sciences), 1998, vol. 48, pp. 155-165.

Hermann, Thomas, Adaptive recognition by nucleic acid aptamers, Science, Feb. 2, 2000, vol. 287, pp. 820-825.

Hermann, Thomas, Chemical and functional diversity of small molecule ligands for RNA, Biopolymers, 2003, vol. 70, pp. 4-18.

Hermann, Thomas, Drugs targeting the ribosome, Current Opinion in Structural Biology, 2005, vol. 15, pp. 355-366.

Hermann, Thomas, Strategies for the Design of Drugs Targeting RNA and RNA-Protein Complexes, Angew Chem Int Ed Engl, 2000, vol. 39, pp. 1890-1904.

Hidalgo, Ismael, Assessing the absorption of new pharmaceuticals, Current Topics in Medicinal Chemistry, 2001, vol. 1, pp. 385-401.

Hofacker et al, Automatic detection of conserved RNA structure elements in complete RNA virus genomes, Nucleic Acids Research, 1998, vol. 26, No. 16, pp. 3825-3826.

Honda et al, A Phylogenetically Conserved Stem-Loop Structure at the 5' Border of the Internal Ribosome Entry Site of Hepatitis C Virus Is Required for Cap-Independent Viral Translation, Journal of Virology, vol. 73, No. 2, pp. 1165-1174, Feb. 1999.

Honda et al, Structural requirements for initiation of translation by internal ribosome entry within genome-length hepatitis C virus RNA, Virology, 1996, vol. 222, pp. 31-42.

Honda, et al, Stability of a stem-loop involving the initiator AUG controls the efficiency of internal initiation of translation on hepatitis C virus RNA, RNA, 1996, vol. 2, pp. 955-968.

Horscroft et al, Replicon cell culture system as a valuable tool in antiviral drug discovery against hepatitis C virus, Antiviral Chemistry & Chemotherapy, 2005. vol. 16, pp. 1-12.

Hysell et al, Synthesis and stability of exocyclic triazine nucleosides, Org. Biomol. Chem., 2005, vol. 3, pp. 2946-2952 (published online Jul. 19, 2005).

Ito et al, Determination of the Secondary Structure of and Cellular Protein Binding to the 3'-Untranslated Region of the Hepatitis C Virus RNA Genome, Journal of Virology, Nov. 1997, vol. 71, No. 11, pp. 8698-8706.

Ito et al, The 3'-Untranslated Region of Hepatitis C Virus RNA Enhances Translation from an Internal Ribosomal Entry Site, Journal of Virology, Nov. 1998, vol. 72, No. 11, pp. 8789-8796.

Jefferson et al, Biaryl guanidine inhibitors of in vitro HCV-IRES activity, Bioorganic & Medicinal Chemistry Letters, 2004, vol. 14, pp. 5139-5143.

Ji et al, Coordinated assembly of human translation initiation complexes by the hepatitis C virus internal ribosome entry site RNA, PNAS, Dec. 7, 2004, vol. 101, No. 49, pp. 16990-16995.

Jones et al, The synthesis of carboxymethyl derivatives of purines and pyrimidines and their condensation with naturally occuring macromolecules, Tetrahedron, 1973, vol. 29, pp. 2293-2296.

Jubin et al, Hepatitis C IRES: translating translation into a therapeutic target, Current Opinion Molecular Therapeutics, 2001, vol. 3, pp. 278-287.

Jubin et al, Hepatitis C Virus Internal Ribosome Entry Site (IRES) Stem Loop IIId Contains a Phylogenetically Conserved GGG Triplet Essential for Translation and Ires Folding, Journal of Virology, Nov. 2000, vol. 74, No. 22, pp. 10430-10437.

Jubin, Ronald, Targeting hepatitis C virus translation: stopping HCV where it starts, Current Opinion Investigational Drugs, 2003, vol. 4, No. 2, pp. 162-167.

Katayama et al, TAN-1057 A~D, New Antibiotics with Potent Antibacterial Activity Against Methicillin-Resistant *Staphylococcus aureus* Taxonomy, Fermentation and Biological Activity, The Journal of Antibiotics, Apr. 1993, vol. 46, No. 4, pp. 606-613.

Kaul and Pilch, Thermodynamics of aminoglycoside-rRNA recognition: the binding of neomycin-class aminoglycosides to the A site of 16S rRNA, Biochemistry, 2002, vol. 41, pp. 7695-7706.

Kieft et al, Crystal structure of an RNA tertiary domain essential to HCV IRES-mediated translation initiation, Natural Structural Biology, May 2002 (published online Apr. 1, 2002), vol. 9, No. 5, pp. 370-374.

Kieft et al, The hepatitis C virus internal ribosome entry site adopts an ion-dependent tertiary fold, J. Mol. Biol., 1999, vol. 292, pp. 513-529.

Kikuchi et al, A hepatitis C virus (HCV) internal ribosome entry site (IRES) domain III-IV-targeted aptamer inhibits translation by binding to an apical loop of domain IIId, Nucleic Acids Research, 2005, vol. 33, No. 2, pp. 683-692.

Kikuchi et al, In vitro selection of RNA aptamers that bind to domain II of HCV IRES, Nucleic Acids Research, Supplement No. 2, 2002, pp. 267-268.

Kikuchi et al, RNA aptamers targeted to domain II of hepatitis C virus IRES that bind to its apical loop region, J Biochem, 2003, vol. 133, pp. 263-270.

Kim et al, Domains I and II in the 5' nontranslated region of the HCV genome are required for RNA replication, Biochemical and Biophysical Research Communications, 2002, vol. 290, pp. 105-112.

Kim et al, NMR study of 100 kDa HCV IRES RNA using segmental isotope labeling, J Am Chem Soc, Jul. 2002, vol. 124, pp. 9338-9339.

Kim et al, Template Requirements for De Novo RNA Synthesis by Hepatitis C Virus Nonstructural Protein 5B Polymerase on the Viral X RNA, Journal of Virology, Jul. 2002, vol. 76, No. 14, pp. 6944-6956.

Klinck et al, A potential RNA drug target in the hepatitis C virus internal ribosomal entry site, RNA, 2000, vol. 6, pp. 1423-1431.

Kolykhalov et al, Identification of a Highly Conserved Sequence Element at the 3' Terminus of Hepatitis C Virus Genome RNA, Journal of Virology, Jun. 1996, vol. 70, No. 6, pp. 3363-3371.

Korf et al, Inhibition of hepatitis C virus translation and subgenomic replication by siRNAs directed against highly conserved HCV sequence and cellular HCV cofactors, J Hepatol, 2005, vol. 43, pp. 225-234.

Lacourciere et al, Mechanism of neomycin and Rev peptide binding to the Rev responsive element of HIV-1 as determined by fluorescence and NMR spectroscopy, Biochemistry, 2000, vol. 39, pp. 5630-5641.

Lafuente et al, Long-range RNA-RNA interactions between distant regions of the hepatitis C virus internal ribosome entry site element, Journal of General Virology, 2002, vol. 83, pp. 1113-1121.

Lanciotti, Robert, Molecular amplification assays for the detection of flaviviruses. Advances in Virus Research, 2003, vol. 61, pp. 67-99.

Lee et al, cis-Acting RNA Signals in the NS5B-Terminal Coding Sequence of the Hepatitis C Virus Genome, Journal of Virology, Oct. 2004, vol. 78. No. 20, pp. 10865-10877.

Leontis et al, Motif prediction in ribosomal RNAs Lessons and prospects for automated motif prediction in homologous RNA molecules, Biochimie, 2002, vol. 84, pp. 961-973.

Lescure et al, Novel Selenoproteins Identified in Silico and in Vivo by Using a Conserved RNA structural Motif, The Journal of Biological Chemistry, Dec. 31, 1999, vol. 274, No. 53, pp. 38147-38154.

Leulliot and Varani, Current topics in RNA-protein recognition: control of specificity and biological function through induced fit and conformational capture, Biochemistry, Jul. 10, 2001, vol. 40, No. 27, 7947-7956.

Li et al, Differential Effects on the Hepatitis C Virus (HCV) Internal Ribosome Entry Site by Vitamin B12 and the HCV Core Protein, Journal of Virology, Nov. 2004, vol. 78, No. 21, pp. 12075-12081.

Llano-Sotelo et al, Aminoglycosides modified by resistance enzymes display diminished binding to the bacterial ribosomal aminoacyl-tRNA site, Apr. 2002, Chemistry & Biology, vol. 9, pp. 455-463.

Lohmann et al, Replication of subgenomic hepatitis C virus RNAs in a hepatoma cell line, Science, Jul. 2, 1999, vol. 285, pp. 110-113.

Lott et al, Vitamin B12 and hepatitis C: Molecular biology and human pathology, PNAS, Apr. 24, 2001, vol. 98, No. 9, pp. 4916-4921.

Lukavsky et al, Structure of HCV IRES domain II determined by NMR. Nature Structural Biology, Dec. 2003, vol. 10, No. 12, pp. 1033-1038.

Lukavsky et al, Structures of two RNA domains essential for hepatitis C virus internal ribosome entry. site function, Nature Structural Biology, Dec. 12, 2000, vol. 7, No. 12, pp. 1105-1110.

Luo, Guangxiang, Cellular proteins bind to the poly(U) tract of the 3' untranslated region of hepatitis C virus RNA genome, Virology, 1999, vol. 256, pp. 105-118.

Lyons et al, Hepatitis C virus internal ribosome entry site RNA contains a tertiary structural element in a functional domain of stem-loop II, Nucleic Acids Research, 2001, vol. 29, No. 12, pp. 2535-2541.

Lytle et al, Domains on the hepatitis C virus internal ribosome entry site for 40s subunit binding, RNA, 2002, vol. 8, pp. 1045-1055.

Martinand-Mari et al, Oligonucleotide-based strategies to inhibit human hepatitis C virus, Oligonucleotides, 2003, vol. 13, pp. 539-548.

Murakami et al, Down-regulation of translation driven by hepatitis C virus internal ribosomal entry site by the 3' untranslated region of RNA, Arch Virol, 2001, vol. 146, pp. 729-741.

NIH Consensus Statement on Management of Hepatitis C: 2002, NIH Consensus and State-of-the-Science Statements, vol. 19, No. 3, Jun. 10-12, 2002, National Institutes of Health.

Noller et al, Structure and function of ribosomal RNA, Biochem Cell Biol, 1995, vol. 73, pp. 997-1009.

Odreman-Macchioli et al, Mutational Analysis of the Different Bulge Regions of Hepatitis C Virus Domain II and Their Influence on Internal Ribosome Entry Site Translational Ability, Nov. 9, 2001, vol. 276, No. 45, pp. 41648-41655.

Ogle et al, Insights into the decoding mechanism from recent ribosome structures, Trends in Biochemical Sciences, May 2003, vol. 28, No. 5, pp. 259-266.

Otto and Puglisi, The pathway of HCV IRES-mediated translation initiation, Cell, Oct. 29, 2004, vol. 119, pp. 369-380.

Papatheodoridis and Cholongitas, Chronic hepatitis C and no response to antiviral therapy: potential current and future therapeutic options, Journal of Viral Hepatitis, 2004, vol. 11, pp. 287-296.

Parker and Steitz, RNA Interactions—Determination of RNA-protein and RNA-ribonucleoprotein interactions by nuclease probing, Methods in Enzymology, 1989, vol. 180, pp. 454-468.

Pavesi et al, RNAProfile: an algorithm for finding conserved secondary structure motifs in unaligned RNA sequences, Nucleic Acids Research, 2004, vol. 32, No. 10, pp. 3258-3269.

Pawlotsky, Jean Michael, Hepatitis C virus genetic variability: pathogenic and clinical implications, Clinics in Liver Disease, 2003, vol. 7, pp. 45-66.

Pawlotsky, Jean Michael, Mechanisms of antiviral treatment efficacy and failure in chronic hepatitis C, Antiviral Research, 2003, vol. 59, pp. 1-11.

Pestova et al, Molecular mechanisms of translation initiation in eukaryotes, PNAS, Jun. 19, 2001, vol. 98, No. 13, pp. 7029-7036.

Pfister et al, The molecular basis for A-site mutations conferring aminoglycoside resistance: relationship between ribosomal susceptibility and X-ray crystal structures, Chembiochem, 2003, vol. 4, pp. 1078-1088.

Plosker and Keating, Peginterferon-alpha-2a (40kD) plus ribavirin: a review of its use in hepatitis C Virus and HIV co-infection, Drugs, 2004, vol. 64, pp. 2823-2843.

Poordad et al, Developments in hepatitis C therapy during 2000-2002. Expert Opinion Emerging Drugs, 2003, vol. 8, No. 1, pp. 9-25.

Poynard et al, Viral hepatitis C, The Lancet, Dec. 20-27, 2003, vol. 362, pp. 2095-2100.

Price et al, Crystallization of RNA-protein complexes I. Methods for the large-scale preparation of RNA suitable for crystallographic studies, J Mol Biol, 1995, vol. 249, pp. 398-408.

Pudi et al, A Peptide Derived from RNA Recognition Motif 2 of Human La Protein Binds to Hepatitis C Virus Internal Ribosome Entry Site, Prevents Ribosomal Assembly, and Inhibits Internal Initiation of Translation, Journal of Virology, Aug. 2005, vol. 79, pp. 9842-9853.

Ray and Das, Inhibition of hepatitis C virus IRES-mediated translation by small RNAs analogous to stem-loop structures of the 5'-untranslated region. Nucleic Acids Research, 2004, vol. 32, pp. 1678-1687 (published online Mar. 12, 2004).

Reigadas et al, An oligonucleotide complementary to the SL-B1 domain in the 3'-end of the minus-strand RNA of the hepatitis C virus inhibits in vitro initiation of RNA synthesis by the viral polymerase, Virology, 2003, vol. 314, pp. 206-220.

Rijnbrand et al, Mutational and structural analysis of stem-loop IIIC of the hepatitis C virus and GB virus B internal ribosome entry sites, J Mol Biol, 2004, vol. 343, pp. 805-817.

Ryan et al, Recognition of the highly conserved GTPase center of 23 S ribosomal RNA by ribosomal protein L11 and the antibiotic thiostrepton, J Mol Biol, 1991, vol. 221, pp. 1257-1268.

Seth et al, SAR by MS: Discovery of a new class of RNA-binding small molecules for the hepatitis C virus: internal ribosome entry site IIa subdomain, J Med Chem, 2005, vol. 48, pp. 7099-7102.

Shandrick et al, Monitoring molecular recognition of the ribosomal decoding site, Angew Chem Int Ed Engl, 2004, vol. 43, pp. 3177-3182.

Simonsen et al, Novel paromamine derivatives exploring shallow-groove recognition of ribosomal-decoding-site RNA, ChemBioChem, 2002, vol. 3, pp. 1223-1228.

Simonsen et al, Piperidine glycosides targeting the ribosomal decoding site, ChemBioChem, 2003 vol. 4, pp. 886-890.

Siridechadilok et al, Structural roles for human translation factor eIF3 in initiation of protein synthesis, Science, Dec. 2, 2005, vol. 310, pp. 1513-1515.

Smith and Simmonds, Characteristics of nucleotide substitution in the hepatitis C virus genome: constraints on sequence change in coding regions at both ends of the genome, Journal of Molecular Evolution, 1997, vol. 45, pp. 238-246.

Smith et al, Secondary structure and hybridization accessibility of hepatitis C virus 3'-terminal sequences, Journal of Virology, Oct. 2002, vol. 76, No. 19, pp. 9563-9574.

Sokolov et al, Total syntheses of TAN-1057 A/B, a new dipeptide antibiotic from *Flexibacter* sp. PK-74, Eur J Org Chem, 1998, pp. 777-783.

Soler et al, Virological effects of ISIS 14803, an antisense oligonucleotide inhibitor of hepatitis C virus (HCV) internal ribosome entry site (IRES), on HCV IRES in chronic hepatitis C patients and examination of the potential role of primary and secondary HCV resistance in the outcome of treatment, Antiviral Therapy, 2004, vol. 9, pp. 953-968.

Spahn et al, Hepatitis C virus IRES RNA-induced changes in the conformation of the 40s ribosomal subunit, Science, 2001, vol. 291, pp. 1959-1962.

Steitz, Thomas, On the structural basis of peptide-bond formation and antibiotic resistance from atomic structures of the large ribosomal subunit, FEBS Letters, 2005, vol. 579, pp. 955-958.

Sucheck and Wong, RNA as a target for small molecules, Current Opinion in Chemical Biology, 2000, vol. 4, pp. 678-686.

Takyar et al, Vitamin B12 stalls the 80 S ribosomal complex on the hepatitis C internal ribosome entry site, J Mol Biol, 2002, vol. 319, pp. 1-8.

Tan et al, Hepatitis C therapeutics: current status and emerging strategies, Nature Reviews—Drug Discovery, Nov. 2002, vol. 1, pp. 867-881.

Thelu et al, Lack of clinical significance of variability in the internal ribosome entry site of hepatitis C virus, Journal of Medical Virology, 2004, vol. 72, pp. 396-405.

Thomson and Finch, Hepatitis C virus infection, European Society of Clinical Microbiology and Infectious Diseases, 2005, vol. 11, pp. 86-94.

Tor et al, Deciphering RNA recognition: aminoglycoside binding to the hammerhead ribozyme, Chemistry & Biology, Nov. 1998, vol. 5, No. 11, pp. R277-R283.

Tsukiyama-Kohara et al, Internal ribosome entry site within hepatitis C virus RNA, Journal of Virology,1992, vol. 66, pp. 1476-1483.

Tuplin et al, Thermodynamic and phylogenetic prediction of RNA secondary structures in the coding region of hepatitis C virus, RNA, 2002, vol. 8, pp. 824-841.

Varaklioti et al, Mutational analysis of two unstructured domains of the 5' untranslated region of HCV RNA, Biochemical and Biophysical Research Communications, 1998, vol. 253, No. 3, pp. 678-685.

Vicens and Westhof, Molecular recognition of aminoglycoside antibiotics by ribosomal RNA and resistance enzymes: an analysis of x-ray crystal structures, Biopolymers, 2003, vol. 70, pp. 42-57.

Vicens and Westhof, RNA as a drug target: the case of aminoglycosides, ChemBioChem, 2003, vol. 4, pp. 1018-1023.

Vourloumis et al, Aminoglycoside-hybrid ligands targeting the ribosomal decoding site. ChemBioChem, 2005, vol. 6, pp. 58-65.

Vourloumis et al, Novel 2,5-dideoxystreptamine derivatives targeting the ribosomal decoding site RNA, Bioorganic and Medicinal Chemistry Letters, 2002, vol. 12, pp. 3367-3372.

Vourloumis et al, Novel acyclic deoxystreptamine mimetics targeting the ribosomal decoding site, ChemBioChem, 2003, vol. 4, pp. 879-885.

Vourloumis et al, Solid-phase synthesis of benzimidazole libraries biased for RNA targets, Tetrahedron Letters, 2003, vol. 44, pp. 2807-2811.

Walker et al, Hepatitis C virus therapies: current treatments, targets and future perspectives, Antiviral Chemistry & Chemotherapy, 2003, vol. 14, pp. 1-21.

Wang et al, A conserved helical element is essential for internal initiation of translation of hepatitis C virus RNA, Journal of Virology, 1994, vol. 68, pp. 7301-7307.

Wang et al, An RNA pseudoknot is an essential structural element of the internal ribosome entry site located within the hepatitis C virus 5' noncoding region, RNA, 1995, vol. 1, pp. 526-537.

Wang et al, Hepatitis C viral IRES inhibition by phenazine and phenazine-like molecules, Bioorganic & Medicinal Chemistry Letters, 2000, vol. 10, pp. 1151-1154.

Wang et al, Translation of human hepatitis C virus RNA in cultured cells is mediated by an internal ribosome-binding mechanism, Journal of Virology, Jun. 1993, vol. 67, No. 6, pp. 3338-3344.

Wilkinson, Trevor, Hepatitis C virus: prospects for future therapies, Current Opinion in Investigational Drugs, 2001, vol. 2, pp. 1516-1522.

Williamson, James, Induced fit in RNA-protein recognition, Nature Structural Biology, Oct. 2000, vol. 7, pp. 834-837.

Wilson and Li, Targeting RNA with small molecules, Current Medicinal Chemistry, 2000, vol. 7, pp. 73-98.

Winkler and Breaker, Regulation of bacterial gene expression by riboswitches, Annual Reviews of Microbiology, 2005, vol. 59, pp. 487-517.

Wood et al, Hepatitis C virus 3'X region interacts with human ribosomal proteins, Journal of Virology, Feb. 2001, vol. 75, pp. 1348-1358.

Wyles et al, Synergy of Small Molecular Inhibitors of Hepatitis C Virus Replication Directed at Multiple Viral Targets, Journal of Virology, Mar. 2007, vol. 81, No. 6, pp. 3005-3008.

Xavier et al, RNA as a drug target: methods for biophysical characterization and screening. TIBTECH, Aug. 2000, vol. 18, pp. 349-356.

Yamada et al, Genetic organization and diversity of the 3' noncoding region of the hepatitis C virus genome, Virology, 1996, vol. 223, article No. 0476, pp. 255-261.

Ye et al, Aminoglycoside mimetics as small-molecule drugs targeting RNA, Current Medicinal Chemistry, 2002, vol. 9, pp. 929-939.

Yi and Lemon, 3' nontranslated RNA signals required for replication of hepatitis C virus RNA, Journal of Virology, Mar. 2003, vol. 77, No. 6, pp. 3557-3568.

Yi and Lemon, Structure-function analysis of the 3' stem-loop of hepatitis C virus genomic RNA and its role in viral RNA replication, RNA, 2003, vol. 9, pp. 331-345.

Yoshizawa et al, Structural origins of gentamicin antibiotic action, The EMBO Journal, 1998, vol. 17, No. 22, pp. 6437-6448.

You et al, A cis-acting replication element in the sequence encoding the NS5B RNA-dependent RNA polymerase is required for hepatitis C virus RNA replication, Journal of Virology, Feb. 2004, vol. 78, No. 3, pp. 1352-1366.

Zhao et al, Molecular Recognition of RNA by Neomycin and a Restricted Neomycin Derivative, Angew Chem Int Ed Engl, 2005, vol. 44, pp. 5329-5334.

Zhou et al, Structure-activity relationships of novel antibacterial translation inhibitors: 3,5-Diamino-piperidinyl triazines, Bioorganic & Medicinal Chemistry Letters, 2006, vol. 16, pp. 5451-5456.

Zhou et al, Structure-guided discovery of novel aminoglycoside mimetics as antibacterial translation inhibitors, Antimicrobial Agents and Chemotherapy, Dec. 2005, vol. 49, No. 12, pp. 4942-4949.

Zhou et al, Synthesis and SAR of 3,5-diamino-piperdine derivatives: Novel antibacterial translation inhimibtors as aminoglycoside mimetics, Bioorganic & Medicinal Chemistry Letters, 2007, vol. 17, pp. 1206-1210.

Remington's Pharmaceutical Sciences, Mack Publishing Co., Easton, PA, 18th edition, 1990, TOC only.

IUPAC-IUB, "Commission on biochemical nomenclature abbreviated nomenclature of synthetic polypeptides (Polymerized Amino Acids)," Biochemistry. 1972; 11: 942-944.

International Preliminary Report on Patentability and Written Opinion mailed Aug. 3, 2010 for International Application No. PCT/US2009/032476, filed Jan. 29, 2009.

ANTIVIRAL COMPOUNDS FOR THE TREATMENT OF HCV INFECTION

RELATED APPLICATIONS

This application is the U.S. National Phase under 35 U.S.C. §371 of International Application No. PCT/US2009/032476, filed Jan. 29, 2009 under the Patent Cooperation Treaty (PCT), designating the United States, and published in English as WO 2009/099897 on Aug. 13, 2009, which claims the benefit of U.S. Provisional Application No. 61/025,264 filed Jan. 31, 2008, the disclosures of which are hereby incorporated herein by reference in their entireties.

STATEMENT OF GOVERNMENT SUPPORT

The present invention was made with government support under the following grants: R01 AI072012 awarded by the National Institute of Health. The government has certain rights in the invention.

BACKGROUND OF THE INVENTION

1. The Field

The present application relates to certain compounds and to methods for the preparation and the use of certain compounds in the fields of chemistry and medicine.

2. Description of the Related Art

Hepatitis C virus (HCV), a positive-strand RNA virus, is a leading cause of chronic liver disease, with over 170 million people infected worldwide. According to the Centers for Disease Control (CDC), chronic HCV infection currently affects more than 3 million Americans and causes 10,000 to 12,000 deaths a year in the United States. The CDC estimates that the annual mortality rate will increase to 38,000 by the year 2010, surpassing the number of deaths attributed annually to HIV/AIDS. HCV infection is also the leading indication for liver transplantation.

There is neither a vaccine nor a direct antiviral drug available to treat or prevent the spread of HCV. The current standard of care for chronic HCV consists of a combination of injected interferon-alpha and the nucleoside analogue ribavirin. The significant side effects associated with both drugs render it difficult to sustain therapy over prolonged periods of time. Many patients require additional drugs to treat adverse effects of interferon, further increasing the cost and the risk of additional side effects. As a result, poor compliance with the course of HCV therapy decreases the patient response rate. Importantly, current HCV therapies are directed at stimulating the immune system but do not directly target the virus. Consequently, sustained virus elimination is not achieved in more than half of the treated patients even after six months of therapy. Therefore, novel drugs are required to treat HCV infection by directly acting on viral targets.

A majority of drug discovery research for HCV has focused on the viral proteins which include structural and nonstructural (NS) targets. Among the latter, the NS3-4A protease and the NS5B RNA-dependent RNA polymerase are in the focus of many antiviral discovery programs, paralleling past efforts in the somewhat corresponding protease and reverse transcriptase targets of human immunodeficiency virus (HIV). As with HIV, the high genetic variability of HCV poses a significant challenge for the development of antiviral mono-therapies. The low fidelity of the HCV NS5B polymerase facilitates the emergence of viral variants, including six major genotypes and a large number of subtypes. Rapid selection of resistant virus populations is expected under mono-therapy treatment regimes. Thus, combination of several drugs to attack distinct viral targets will be mandatory for successful HCV therapy.

Since the HCV genome contains several highly conserved cis-acting RNA elements, the repertoire of protein targets for antiviral intervention may be expanded by RNA targets. Structured functional elements of the HCV genome that are candidate drug targets have been identified in the 5' and 3' nontranslated regions (NTR) and in the coding region of the NS5B polymerase.

The 5' NTR stretches over 341 nt of which the first 40 are essential for RNA replication. The 330 nt region immediately flanking the reading frame for the viral genes contains an internal ribosome entry site (IRES) which mediates translation initiation of the viral message via a 5' cap-independent mechanism. The IRES RNA binds directly to the host cell 40S ribosomal subunit and initiates protein translation in the absence of most initiation factors. Recruitment of the small ribosomal subunit to the HCV message is driven entirely through the high affinity of the IRES RNA-40S interaction. The IRES RNA sequence is one of the most conserved regions of the entire viral genome and adopts a highly ordered secondary structure.

Most of the IRES subdomains are critical for translation initiation, including the stem-loops, a helix between subdomains II and III, a proposed pseudoknot involving loop IIIf and the single-stranded regions that flank subdomain IIb, and a stem-loop containing the start AUG codon. The three-dimensional architecture of the IRES RNA is dominated by the independently-folding subdomains that adopt specific folds in the presence of physiological concentrations of metal ions. Since the single-stranded stretches between the subdomains are flexible, the IRES element becomes three-dimensionally ordered only after binding to the 40S ribosomal subunit. Three-dimensional structures of individual subdomains have been determined by crystallography and NMR, including the subdomains II and IIIa-e which revealed unique RNA architectures that might be exploited for small-molecule recognition. Based on its importance for viral replication and its high conservation the HCV IRES element has been discussed as a potential target for therapeutic intervention. For example, it has been observed that mutational stabilization of stem-loop IV, which contains the initiator AUG codon of the HCV polyprotein, prevented translation of the viral mRNA, suggesting an approach for the development of IRES RNA-stabilizing ligands as antivirals. Validation studies on the IRES target have been performed using antisense, aptamer, ribozyme and siRNA approaches. At least one peptide and three classes of small-molecules have been described as inhibitors of in vitro IRES activity, including biaryl guanidines, phenazine derivatives, and vitamin B12.

The 3' NTR is comprised of three distinct domains including a 40-nt variable region, a downstream poly(U/C) tract of heterogeneous length, and a highly conserved 98-nt segment termed X-region. Both the poly(U/C) tract and the X-region are essential for RNA replication but not for translation. Secondary structure prediction, phylogenetic analyses, as well as nuclease probing suggest that the X-region folds into three stem-loops which are the most conserved RNA sequences in the HCV 3'-NTR. It has been suggested that specifically stem-loop 1 is involved in replication by providing binding sites for the viral NS3 protease/helicase and NS5B polymerase. Cellular factors, including polypyrimidine tract-binding protein (PTB) and ribosomal proteins, have been shown to interact with the X-region RNA, thereby interfering with the binding of viral proteins and participating in the regulation of viral translation. The stem-loops 2 and 3 were mapped as essential parts of the PTB binding site. The highly conserved secondary structure of the X-region as well as its importance for RNA replication and as binding site for viral and host proteins have led to suggestions to exploit the 3' NTR as a target for antiviral agents including antisense oligonucleotides.

Evidence has emerged that stem-loop 2 in the X-region might participate in a pseudoknot interaction with a conserved RNA element within the coding region of the viral NS5B polymerase. Earlier phylogenetic and RNA folding analyses suggested the presence of several stem-loop structures within the NS5B coding region. Four of the predicted stem-loops that are located within a highly conserved region of the HCV genome were confirmed by mutational and biochemical analyses. The secondary structure of stem-loop V (5BSL3.2) was also confirmed by NMR spectroscopy. The stem-loops V and VI are essential for viral RNA replication and thus constitute cis-acting replication elements (CRE) which are similar to cis-acting RNA structures found in the genomes of other RNA viruses. The HCV NS5B polymerase, which has been shown to interact with 3' viral genomic RNA, binds specifically to SL-V. While the precise function of the SL-V RNA element has yet to be determined, the role it plays in viral replication is dependent on its location within the HCV genome. This context dependence of SL-V function is likely to be related to a kissing interaction between the apical hairpin loops of SL-V and SL-2 in the HCV X-region which gives rise to a pseudoknot structure involving coding region and 3' NTR of the viral genome. It has been speculated that formation of a replication-essential pseudoknot might include interactions with NS5B polymerase. Despite the current lack of extensive functional insight into the role of conserved RNA elements in the NS5B coding region, the essentiality of these CRE for viral replication renders them promising targets for RNA-directed antiviral drugs.

SUMMARY OF THE APPLICATION

In some embodiments, compounds for treating HCV are provided. Certain embodiments relate to methods of treating HCV in animals. The method can include, for example, administering an effective amount of a compound to a patient in need thereof. Other embodiments relate to the use of compounds in the manufacture of a pharmaceutical or medicament for the treatment of HCV.

In some embodiments, the present application discloses a compound of Formula (I):

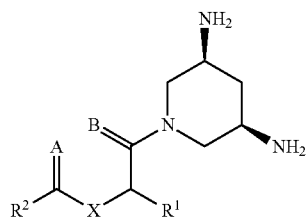

(I)

wherein:
X is NH, O, S, or $(CH_2)_{n1}$, wherein $n_1$ is 1 to 6;
A is O or S;
B is O or S;
each $R^1$ and $R^2$, independently, is $-CONH_2$, or a substituted or unsubstituted $C_{1-6}$ alkyl, a substituted or unsubstituted aryl, a substituted or unsubstituted heteroaryl, a substituted or unsubstituted $-(CH_2)_n$ aryl, a substituted or unsubstituted $-(CH_2)_n$ heteroaryl, a substituted or unsubstituted $-(CH_2)_n$ heterocycloalkyl, a substituted or unsubstituted $-(CH=CH)_n$ aryl, a substituted or unsubstituted $-(CH=CH)_n$ heteroaryl, a substituted or unsubstituted $-C_{2-6}$ alkenyl-aryl, a substituted or unsubstituted $-C_{2-6}$ alkenyl-heteroaryl, a substituted or unsubstituted $-(C\equiv C)_n$ aryl, a substituted or unsubstituted $-(C\equiv C)_n$ heteroaryl, a substituted or unsubstituted $-NR^3-C_{1-6}$ alkyl, a substituted or unsubstituted $-NR^3$-aryl, a substituted or unsubstituted $-NR^3$-heteroaryl, a substituted or unsubstituted $-NR^3$-cycloalkyl, a substituted or unsubstituted $-NR^3$-heterocycloalkyl, a substituted or unsubstituted $-NHNH-C_{1-6}$ alkyl, a substituted or unsubstituted $-NHNH$-aryl, a substituted or unsubstituted $-NHNH$-heteroaryl, a substituted or unsubstituted $-NHNH$-cycloalkyl, a substituted or unsubstituted $-NHNH$-heterocycloalkyl, a substituted or unsubstituted $-O-C_{1-6}$ alkyl, a substituted or unsubstituted $-O$-aryl, a substituted or unsubstituted $-O$-heteroaryl, a substituted or unsubstituted $-O$-cycloalkyl, a substituted or unsubstituted $-O$-heterocycloalkyl, $-S(C_{1-6})$ alkyl, a substituted or unsubstituted $-S$-aryl, a substituted or unsubstituted $-S$-heteroaryl, a substituted or unsubstituted $-S$-cycloalkyl, a substituted or unsubstituted $-S$-heterocycloalkyl, a substituted or unsubstituted $-(C=O)(C_{1-6})$ alkyl, a substituted or unsubstituted $-(C=O)$ aryl, a substituted or unsubstituted $-(C=O)$ heterocycloalkyl, n being an integer from 1 to 4; and $R^3$ is $-H$ or a substituted or unsubstituted alkyl, aryl, heteroaryl, cycloalkyl, or heterocycloalkyl.

In other embodiments, the present application discloses a compound of Formula (II):

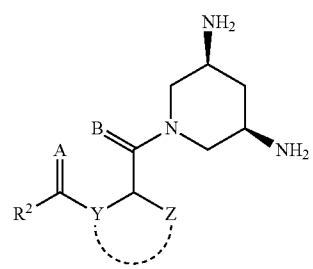

II wherein:
A is O or S;
B is O or S;
Y is N or CH, or $-(CH_2)_{n2}CH-$, wherein $n_2$ is from 1 to 6;
Z is a lower alkylene group or a lower heteroalkylene group such that Z and Y together with the C atom between them form a 4-, 5-, or 6-membered substituted or unsubstituted cycloalkyl or heterocycloalkyl.

each $R^2$ is $-CONH_2$, or a substituted or unsubstituted $-C_{1-6}$ alkyl, a substituted or unsubstituted aryl, a substituted or unsubstituted heteroaryl, a substituted or unsubstituted $-(CH_2)_n$ aryl, a substituted or unsubstituted $-(CH_2)_n$ heteroaryl, a substituted or unsubstituted $-(CH_2)_n$ heterocycloalkyl, a substituted or unsubstituted $-(CH=CH)_n$ aryl, a substituted or unsubstituted $-(CH=CH)_n$ heteroaryl, a substituted or unsubstituted $-C_{2-6}$ alkenyl-aryl, a substituted or unsubstituted $-C_{2-6}$ alkenyl-heteroaryl, a substituted or unsubstituted $-(C\equiv C)_n$ aryl, a substituted or unsubstituted $-(C\equiv C)_n$ heteroaryl, a substituted or unsubstituted $-NR^3-C_{1-6}$ alkyl, a substituted or unsubstituted $-NR^3$- aryl, a substituted or unsubstituted —NR³-heteroaryl, a substituted or unsubstituted —NR³-cycloalkyl, a substituted or unsubstituted —NR³-heterocycloalkyl, a substituted or unsubstituted —NHNH—C$_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—C$_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, a substituted or unsubstituted —S(C$_{1-6}$) alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C═O)(C$_{1-6}$) alkyl, a substituted or unsubstituted —(C═O) aryl, a substituted or unsubstituted —(C═O) heterocycloalkyl, n being an integer from 1 to 4; and R³ is —H or a substituted or unsubstituted alkyl, aryl, heteroaryl, cycloalkyl, or heterocycloalkyl.

Further embodiments relate to a compound of Formula (III), where the compound is:

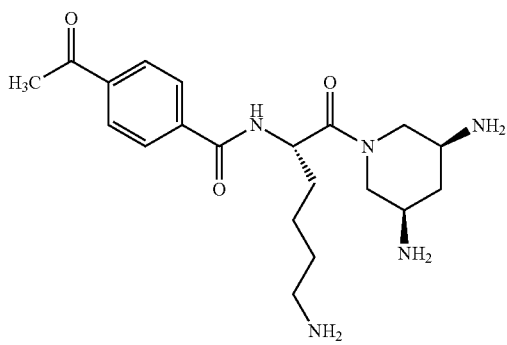 [SMILES: CC(=O)c1ccc(C(=O)N[C@@H](CCCCN)C(=O)N2C[C@H](N)C[C@H](N)C2)cc1]

In another preferred embodiment, a pharmaceutical composition comprising a pharmaceutically acceptable carrier and an effective amount of a compound of Formula (I) or a pharmaceutically acceptable salt thereof is disclosed.

In another preferred embodiment, pharmaceutical composition comprising a pharmaceutically acceptable carrier and an effective amount of a compound of Formula (II) or a pharmaceutically acceptable salt thereof is disclosed.

In other embodiments, a method of inhibiting an HCV infection comprising administering a therapeutically effective amount of a compound of Formula (I) to an individual having an HCV infection is disclosed In further embodiments, a method of inhibiting an HCV infection comprising administering a therapeutically effective amount of a compound of Formula (II) to an individual having an HCV infection is disclosed.

In additional embodiments, a method of synthesis of a compound comprising: obtaining an amino acid; protecting the amino acid to obtain amino-protected α-amino carboxylic acids; reacting the amino-protected α-amino carboxylic acids with

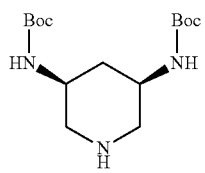 [SMILES: CC(C)(C)OC(=O)N[C@@H]1CNC[C@H](NC(=O)OC(C)(C)C)C1]

to form

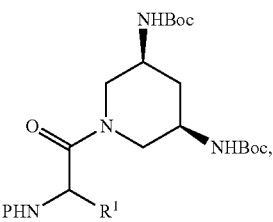

wherein P is a protecting group; deprotecting

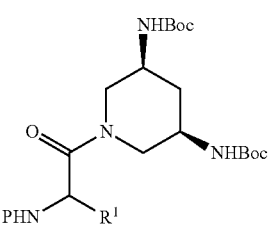

and reacting with

to form:

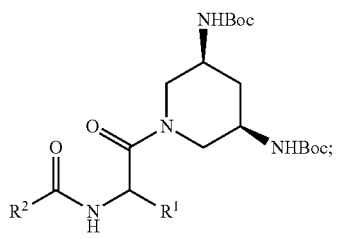

and deprotecting

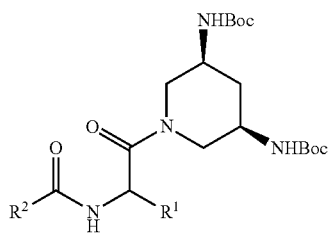

to form the compound.

BRIEF DESCRIPTION OF THE DRAWINGS

The accompanying drawings, which are incorporated in and form part of the specification, merely illustrate certain preferred embodiments of the present application. Together with the remainder of the specification, they are meant to serve to explain preferred modes of making certain compounds of the application to those of skilled in the art. In the drawings.

DETAILED DESCRIPTION OF THE PREFERRED EMBODIMENT

Figure 1A:
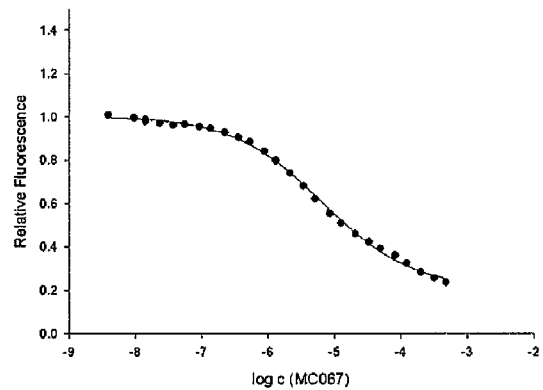
FIG. 1A is a diagram showing a binding curve of Formula I-A. Compound binding is measured in vitro as decrease in fluorescence of a fluorescently labeled HCV IRES RNA fragment upon titration with increasing amounts of compound.
Figure 1B:
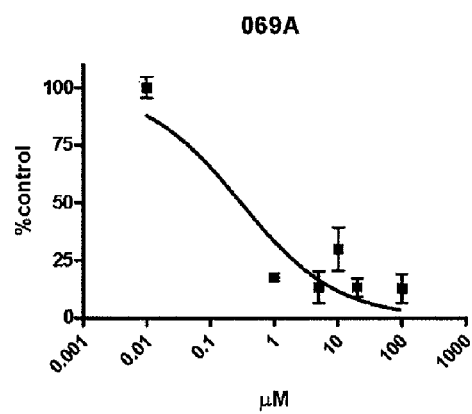
FIG. 1B is a diagram showing inhibition of HCV by Formula III in a subgenomic replicon.

It has been shown that the chemical compounds described herein have antiviral activity as inhibitors of hepatitis C virus (HCV) protein synthesis. The compounds described herein target a structured ribonucleic acid (RNA) target that is unique to the HCV genome and that is essential for the initiation of viral protein synthesis. In one embodiment, the RNA target may be the internal ribosome entry site (IRES) of HCV. The compounds described herein can bind to a subdomain of the HCV IRES RNA, the structure of which can be determined by X-ray crystallography. Binding of selected examples of the compounds described herein to HCV IRES RNA has been demonstrated. HCV inhibitory activity of at least one of the compounds described herein that bind to the HCV IRES RNA has been demonstrated in a cellular assay (subgenomic HCV replicon). It has been shown that the compounds described herein have no or low cytotoxicity at concentrations that are sufficient to inhibit viral replication.

The compounds described herein target a structured viral RNA that is highly conserved among clinical HCV isolates. In some embodiments, the compounds described herein may target viral proteins. In other embodiments, the compounds may be used as inhibitors of HCV infection. The compounds described herein can penetrate HCV-infected cells, bind to HCV IRES RNA and interfere with the function of the IRES during HCV protein translation.

DEFINITIONS

Unless defined otherwise, all technical and scientific terms used herein have the same meaning as is commonly understood by one of ordinary skill in the art to which this application belongs. All patents, applications, published applications and other publications referenced herein are incorporated by reference in their entirety. In the event that there are plurality of definitions for a term herein, those in this section prevail unless stated otherwise As used herein, any "R" group(s) represent substituents that can be attached to the indicated atom.

Whenever a group of this application is described as being "optionally substituted" that group may be unsubstituted or substituted with one or more of the indicated substituents. Likewise, when a group is described as being "unsubstituted or substituted" if substituted, the substituent may be selected from one of more the indicated substituents.

Unless otherwise indicated, when a substituent is deemed to be "optionally substituted," or "substituted" it is meant that the specified moiety has one or more substituents independently selected from the following group: halogens, $=O$, $=S$, $-C\equiv N$, $-NO_2$, $=NH$, $-NHOH$, $-OH$, $-C(=O)H$, $-C(=NH)NH_2$, $-C(=NH)NHR^4$, $-NH_2$, $-NHR^4$, $-NHC(=NH)NH_2$, $-NHC(=NH)NHR^4$, $-NHC(=O)NH_2$, $-NHC(=O)NHR^4$, $-C(=O)NH_2$, $-C(=O)NHR^4$, $-OC(=O)NH_2$, $-OC(=O)NHR^4$, $-C(=S)NH_2$, $-C(=S)NHR^4$, $-NHC(=S)NH_2$, $-NHC(=S)NHR^4$, $-S(O2)H$, $-S(=O)H$, $-OS(O_2)H$, $-OS(=O)H$, $-C(=O)OH$, $-C(=S)OH$, $-S(O_2)NH_2$, $-S(O_2)NHR^4$, $-S(=O)NH_2$, $-S(=O)NHR^4$, wherein $R^4$ is a substituted or unsubstituted alkyl, aryl, heteroaryl, cycloalkyl, or heterocycloalkyl.

As used herein, "alkyl" refers to a straight or branched hydrocarbon chain fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

As used herein, "alkenyl" refers to an alkyl group that contains in the straight or branched hydrocarbon chain one or more double bonds. An alkenyl group of this application may be unsubstituted or substituted. When substituted, the substituent(s) may be selected from the same groups disclosed above with regard to alkyl group substitution.

As used herein, "aryl" refers to a carbocyclic (all carbon) ring or two or more fused rings (rings that share two adjacent carbon atoms) that have a fully delocalized pi-electron system. Examples of aryl groups include, but are not limited to, benzene, naphthalene and azulene. An aryl group of this application may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "heteroaryl" refers to a monocyclic or multicyclic aromatic ring system (a ring system with fully delocalized pi-electron system), one or two or more fused rings that contain(s) one or more heteroatoms, that is, an element other than carbon, including but not limited to, nitrogen, oxygen and sulfur. Examples of heteroaryl rings include, but are not limited to, furan, thiophene, phthalazinone, pyrrole, oxazole, thiazole, imidazole, pyrazole, isoxazole, isothiazole, triazole, thiadiazole, pyran, pyridine, pyridazine, pyrimidine, pyrazine and triazine. A heteroaryl group of this application may be substituted or unsubstituted. When substituted, hydrogen atoms are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof.

As used herein, "cycloalkyl" refers to a completely saturated (no double bonds) mono- or multi-cyclic hydrocarbon ring system. When composed of two or more rings, the rings may be joined together in a fused, bridged or spiro-connected fashion. Cycloalkyl groups of this application may range from $C_3$ to $C_{10}$, in other embodiments it may range from $C_3$ to $C_6$. A cycloalkyl group may be unsubstituted or substituted. Typical cycloalkyl groups include, but are in no way limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated.

As used herein, "heterocycloalkyl" refers to a completely saturated (no double bonds) mono- or multi-cyclic hydrocarbon ring system. Heterocycloalkyls contain(s) one or more heteroatoms, that is, an element other than carbon, including but not limited to, nitrogen, oxygen and sulfur, which can replace $CH_2$ in the ring system.

The term "lower alkylene group" refers to a straight-chained saturated hydrocarbon tethering group, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$(CH_2)_4$—) groups. A lower alkylene group may be substituted or unsubstituted.

The term "lower heteroalkylene group" refers to a straight-chained tethering group, forming bonds to connect molecular fragments via their terminal atoms. Lower heteroalkylene groups are saturated hydrocarbons that contain(s) one or more heteroatoms, that is, an element other than carbon, including but not limited to, nitrogen, oxygen and sulfur, in place of a methylene group. Examples include, but are not limited to, —$(CH_2)_4$—O—$CH_2$—, —O—$(CH_2)_4$—, and —O—$(CH_2)_2$—S—$CH_2$—.

As used herein, "halo" or "halogen" refers to F (fluoro), Cl (chloro), Br (bromo) or I (iodo).

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

It is understood that, in any compound of this application having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound of this application having one or more double bond(s) generating geometrical isomers that can be defined as E or Z each double bond may independently be E or Z a mixture thereof. Likewise, all tautomeric forms are also intended to be included.

As used herein, "pharmaceutically acceptable salt" refers to a salt of a compound that does not cause significant irritation to a patient to which it is administered and does not abrogate the biological activity and properties of the compound. Pharmaceutical salts can be obtained by reaction of a compound disclosed herein with an acid or base. Base-formed salts include, without limitation, ammonium salt ($NH_4^+$); alkali metal, such as, without limitation, sodium or potassium, salts; alkaline earth, such as, without limitation, calcium or magnesium, salts; salts of organic bases such as, without limitation, dicyclohexylamine, N-methyl-D-glucamine, tris(hydroxymethyl)methylamine; and salts with the amino group of amino acids such as, without limitation, arginine and lysine. Useful acid-based salts include, without limitation, hydrochlorides, hydrobromides, sulfates, nitrates, phosphates, methanesulfonates, ethanesulfonates, p-toluenesulfonates and salicylates.

Pharmaceutically acceptable solvates and hydrates are complexes of a compound with one or more solvent of water molecules, or 1 to about 100, or 1 to about 10, or one to about 2, 3 or 4, solvent or water molecules.

Compounds of Formula I

According to one embodiment, the present application provides compounds of Formula (I):

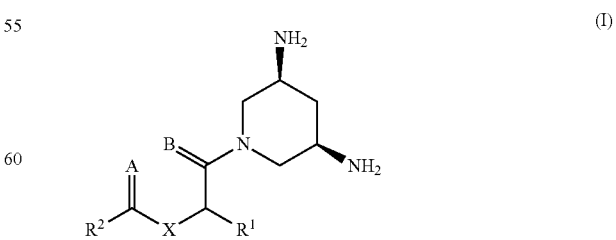

(I)

wherein:
X is NH, O, S, or $(CH_2)_{n1}$, wherein $n_1$ is 1 to 6;
A is O or S;

B is O or S;

each $R^1$ and $R^2$, independently, is —$CONH_2$, or a substituted or unsubstituted —$C_{1-6}$ alkyl, a substituted or unsubstituted aryl, a substituted or unsubstituted heteroaryl, a substituted or unsubstituted —$(CH_2)_n$ aryl, a substituted or unsubstituted —$(CH_2)_n$ heteroaryl, a substituted or unsubstituted —$(CH_2)_n$ heterocycloalkyl, a substituted or unsubstituted —$(CH=CH)_n$ aryl, a substituted or unsubstituted —$(CH=CH)_n$ heteroaryl, a substituted or unsubstituted —$C_{2-6}$ alkenyl-aryl, a substituted or unsubstituted —$C_{2-6}$ alkenyl-heteroaryl, a substituted or unsubstituted —$(C\equiv C)_n$ aryl, a substituted or unsubstituted —$(C\equiv C)_n$ heteroaryl, a substituted or unsubstituted —$NR^3$—$C_{1-6}$ alkyl, a substituted or unsubstituted —$NR^3$-aryl, a substituted or unsubstituted —$NR^3$-heteroaryl, a substituted or unsubstituted —$NR^3$-cycloalkyl, a substituted or unsubstituted —$NR^3$-heterocycloalkyl, a substituted or unsubstituted —NHNH—$C_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—$C_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, —$S(C_{1-6})$ alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C=O)($C_{1-6}$) alkyl, a substituted or unsubstituted —(C=O) aryl, a substituted or unsubstituted —(C=O) heterocycloalkyl, n being an integer from 1 to 4; and $R^3$ is —H or a substituted or unsubstituted alkyl, aryl, heteroaryl, cycloalkyl, or heterocycloalkyl.

According to a preferred series of embodiments, X is NH.

According to another preferred series of embodiments, X is $CH_2$.

According to preferred embodiments, $R^1$ is:

—$(CH_2)_{n3}$—$NH_2$, where $n_3$ is 1 to 6

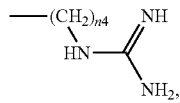

where $n_4$ is 1 to 5

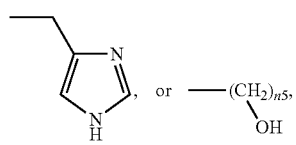

where $n_5$ is 1 to 3

According to preferred embodiments, $R^2$ is:

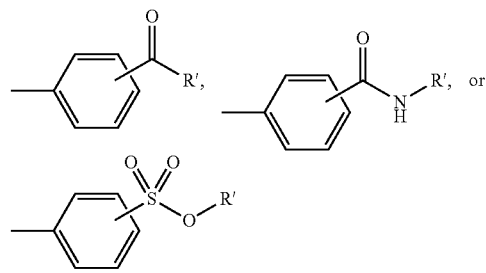

, wherein R' is an alkyl, aryl, heteroaryl, heterycycloalkyl, alkenyl-aryl, cycloalkyl, or alkenyl-heteroaryl According to other preferred embodiments, $R^1$ is:

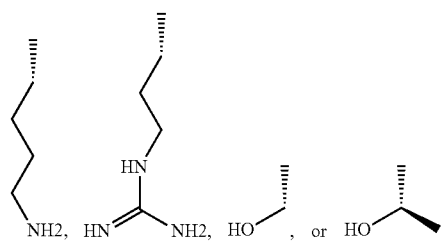

According to other preferred embodiments, $R^2$ is:

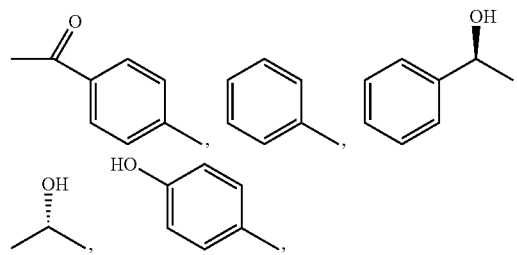

or H.

According to another embodiment, the present application provides compounds of Formula (II):

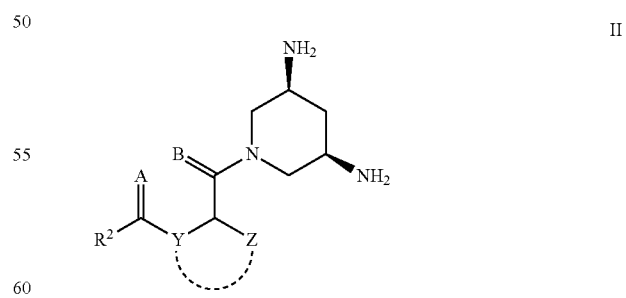

wherein:
A is O or S;
B is O or S;
Y is N or CH, or —$(CH_2)_{n2}CH$—, wherein $n_2$ is from 1 to 6;

Z is a lower alkylene group or a lower heteroalkylene group such that Z and Y together with the C atom between them form a 4-, 5-, or 6-membered substituted or unsubstituted cycloalkyl or heterocycloalkyl.

each $R^2$ is —$CONH_2$, or a substituted or unsubstituted —$C_{1-6}$ alkyl, a substituted or unsubstituted aryl, a substituted or unsubstituted heteroaryl, a substituted or unsubstituted —$(CH_2)_n$ aryl, a substituted or unsubstituted —$(CH_2)_n$ heteroaryl, a substituted or unsubstituted —$(CH_2)_n$ heterocycloalkyl, a substituted or unsubstituted —$(CH═CH)_n$ aryl, a substituted or unsubstituted —$(CH═CH)_n$ heteroaryl, a substituted or unsubstituted —$C_{2-6}$ alkenyl-aryl, a substituted or unsubstituted —$C_{2-6}$ alkenyl-heteroaryl, a substituted or unsubstituted —$(C≡C)_n$ aryl, a substituted or unsubstituted —$(C≡C)_n$ heteroaryl, a substituted or unsubstituted —$NR^3$—$C_{1-6}$ alkyl, a substituted or unsubstituted —$NR^3$-aryl, a substituted or unsubstituted —$NR^3$-heteroaryl, a substituted or unsubstituted —$NR^3$-cycloalkyl, a substituted or unsubstituted —$NR^3$-heterocycloalkyl, a substituted or unsubstituted —NHNH—$C_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—$C_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, a substituted or unsubstituted —$S(C_{1-6})$ alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C═O)($C_{1-6}$) alkyl, a substituted or unsubstituted —(C═O) aryl, a substituted or unsubstituted —(C═O) heterocycloalkyl, n being an integer from 1 to 4; and $R^3$ is —H or a substituted or unsubstituted alkyl, aryl, heteroaryl, cycloalkyl, or heterocycloalkyl.

In preferred embodiments, the compounds of the present application can be represented in Formula (III):

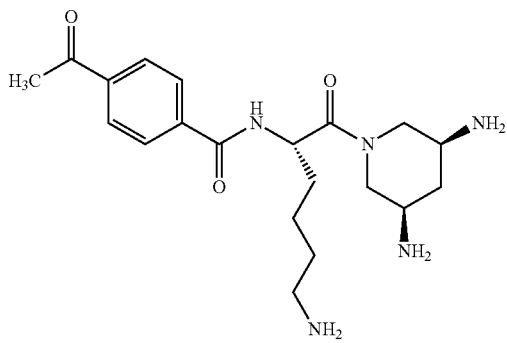

Formula III

In another preferred embodiment, the compound of Formula (I) is present, wherein $R^1$ is

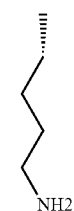

and $R^2$ is

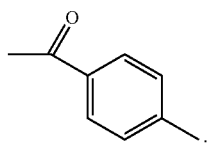

In preferred embodiments, the compound of Formula (I) is present, wherein $R^1$ is

and $R^2$ is

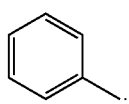

In other preferred embodiments, the compound of Formula (I) is present, wherein $R^1$ is

and $R^2$ is

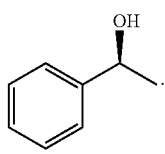

In other preferred embodiments, the compound of Formula (I) is present, wherein $R^1$ is

and R² is

In other preferred embodiments, the compound of Formula (I) is present, wherein R¹ is

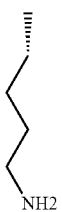

and R² is

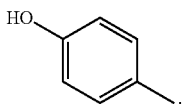

In other preferred embodiments, the compound of Formula (I) is present, wherein R¹ is

and R² is H.

In another preferred embodiment, the compound of Formula (I) is present, wherein R¹ is

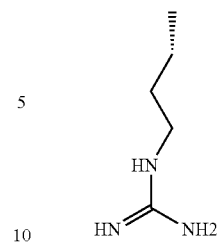

and R² is

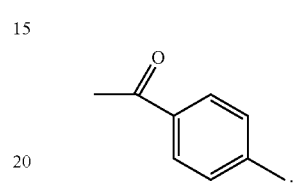

In preferred embodiments, the compound of Formula (I) is present, wherein R¹ is

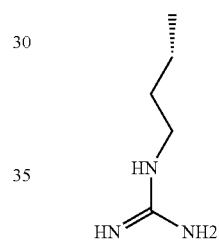

and R² is

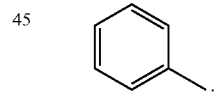

In other preferred embodiments, the compound of Formula (I) is present, wherein R¹ is

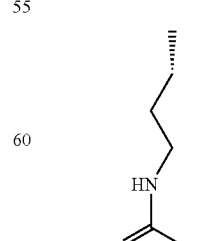

and R² is

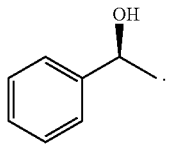

In other preferred embodiments, the compound of Formula (I) is present, wherein R¹ is

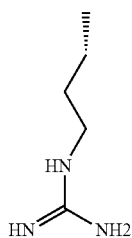

and R² is

In other preferred embodiments, the compound of Formula (I) is present, wherein R¹ is

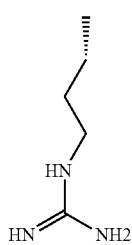

and R² is

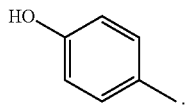

In other preferred embodiments, the compound of Formula (I) is present, wherein R¹ is

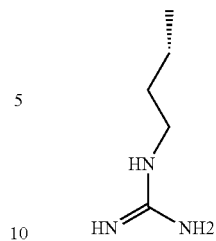

and R² is H.

In another preferred embodiment, the compound of Formula (I) is present, wherein R¹ is

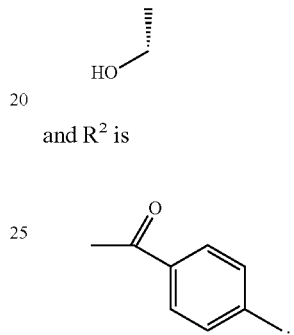

and R² is

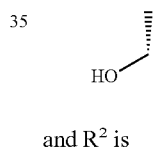

In preferred embodiments, the compound of Formula (I) is present, wherein R¹ is

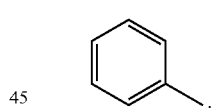

and R² is

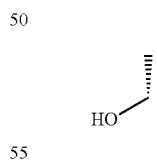

In other preferred embodiments, the compound of Formula (I) is present, wherein R¹ is

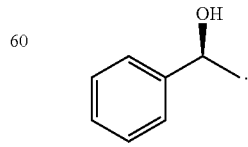

and R² is

In other preferred embodiments, the compound of Formula (I) is present, wherein R¹ is

and R² is

In other preferred embodiments, the compound of Formula (I) is present, wherein R¹ is

and R² is

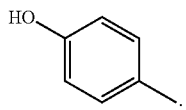

In other preferred embodiments, the compound of Formula (I) is present, wherein R¹ is

and R² is H.

In another preferred embodiment, the compound of Formula (I) is present, wherein R¹ is

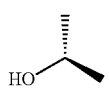

and R² is

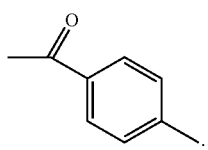

In preferred embodiments, the compound of Formula (I) is present, wherein R¹ is and R² is

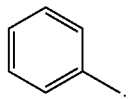

In other preferred embodiments, the compound of Formula (I) is present, wherein R¹ is

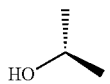

and R² is

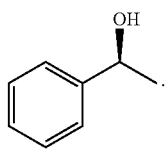

In other preferred embodiments, the compound of Formula (I) is present, wherein R¹ is

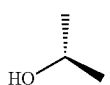

and R² is

In other preferred embodiments, the compound of Formula (I) is present, wherein R¹ is

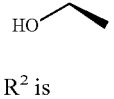

and R² is

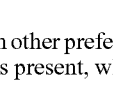

In other preferred embodiments, the compound of Formula (I) is present, wherein R¹ is

and R² is H.

Synthesis of Compounds

In one embodiment, the synthesis of the compounds described herein may be carried out through the following process:

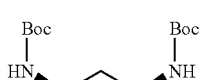
2a protect ↓

2

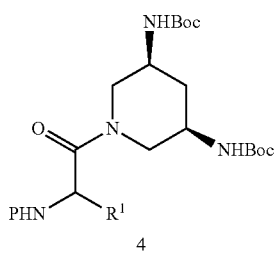
4 a deprotect
b 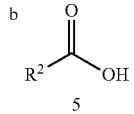
5

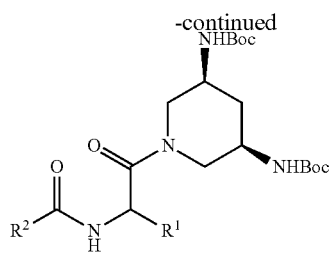
6 deprotect →

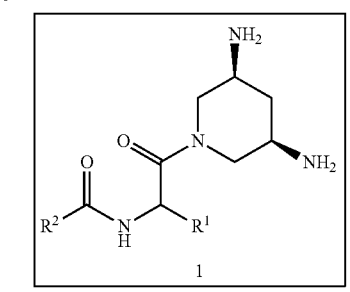
1

In one embodiment, the starting materials can be amino-protected α-amino carboxylic acids that are commercially available or can be prepared from commercially available α-amino acids. During the synthesis, any carboxylic acid may be used as a building block. A list of synthesized compounds can be found in Table 1. Synthesized compounds in Table 1 are identified by the letter of the amino acid building block, wherein K is Lys, R is Arg, S is Ser and T is Thr, and the number of the building blocks, wherein 1 is 4-acetylbenzoic acid, 2 is benzoic acid, 3 is mandelic acid, 4 is lactic acid, 6 is 4-hydroxybenzoic acid and 6 is H. Furthermore, compounds that may be synthesized following the same established procedures are enclosed in parenthesis.

TABLE 1

| amino acid 2a → / ↓ 5 | Lys | Arg | Ser | Thr |
|---|---|---|---|---|
| 1 (4-acetylbenzoic acid) | MC069A (=K1) | R1 | S1 | T1 |
| 2 (benzoic acid) | K2 | R2 | S2 | T2 |

TABLE 1-continued

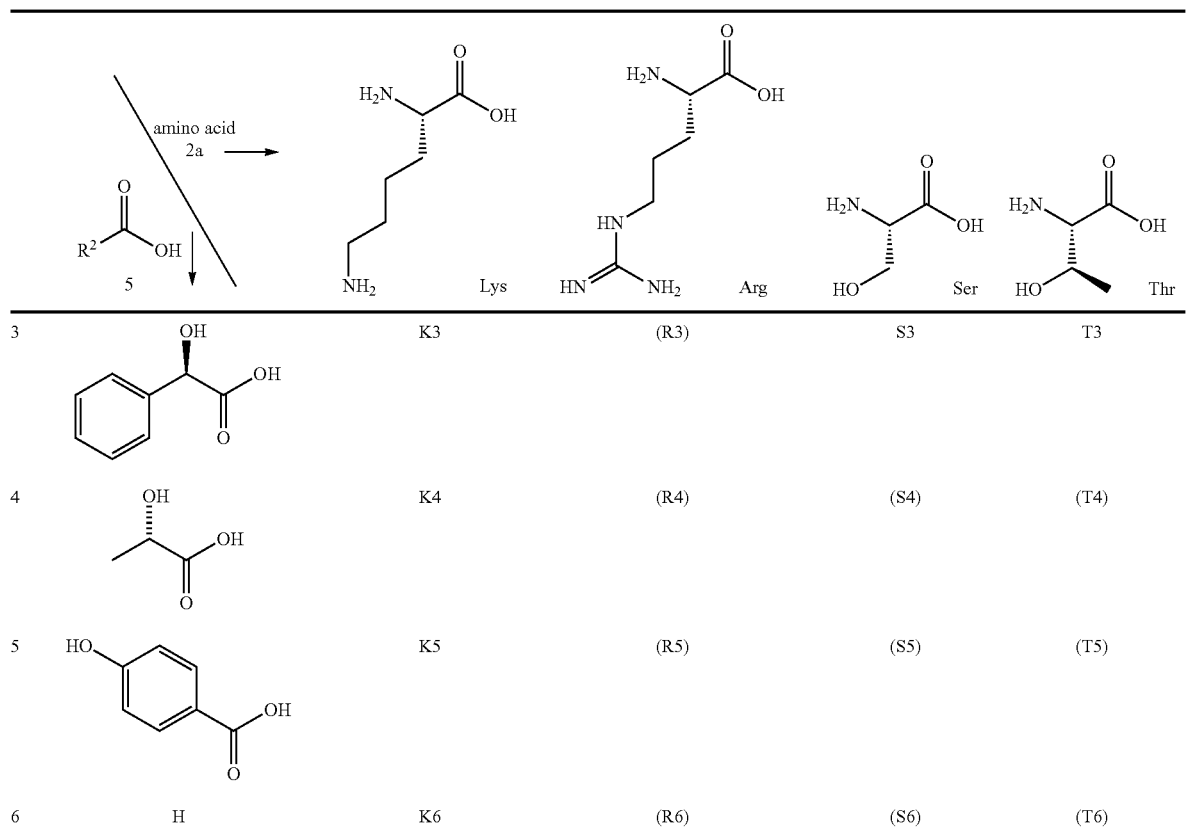

The three principal HCV RNA targets (IRES, NS5B-SLS, and X-region) can be dissected into potentially autonomous fragments for further prioritization based on secondary structure, phylogenetic data, sequence conservation, biological importance, presence of potential ligand binding sites, and suitability for assay development as well as crystallization. The chosen target fragments can be experimentally validated as autonomously folding, stable RNA domains which can further be used for structure determination by X-ray crystallography and affinity assay development.

In parallel, small molecules can be selected from among commercially available known RNA binders ("tool compounds"). New RNA-"friendly" ligands can be designed and synthesized. Validated RNA target fragments can be used for affinity assay development and crystallization. Functional assays can be developed to test ligands for their potential to block HCV-specific processes. Biological assays can be established that use mammalian cell-based systems to measure permeability, general cytotoxicity and antiviral potency of compounds.

Tool compounds and newly synthesized molecules can be screened for binding at the validated RNA target fragments. The identified small-molecule ligands can be further tested in HCV functional and biological assays and submitted to co-crystallization with their respective RNA targets. RNA-ligand complexes can be characterized in solution. Their three-dimensional structure can be determined by X-ray crystallography. Structural information along with binding affinities, inhibitory potencies from functional and antiviral testing, mammalian cytotoxicity as well as permeability data can be used to establish structure-activity relationships for the RNA binders. This data can allow the design of improved ligands for the RNA targets. The suggested ligand discovery process targets is iterative and can ultimately result in lead structures as a basis for the future development of drugs to treat HCV infection.

Assays to Measure Compound Binding

Figure 1C:
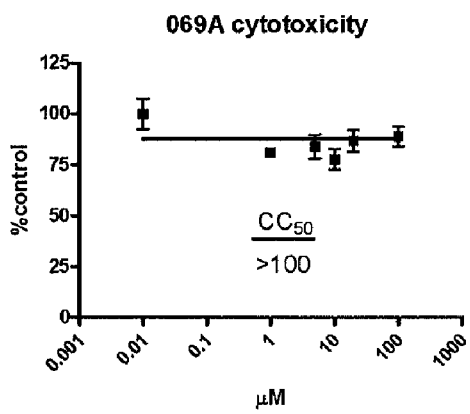
FIG. 1C is a diagram showing inhibition of HCV by Formula III in a cytotoxicity assay.

Fluorescence affinity assays were used to measure compound binding to sub-domain IIa of the HVC IRES. Guided by the crystal structure, a key adenine residue (A54) has previously been identified in the internal loop region of sub-domain IIa of the HCV internal ribosome entry site (IRES) for replacement by the fluorescent nucleobase analog 2-aminopurine (2AP) to monitor ligand binding as well as RNA folding. (ref.: Dibrov, S. M., Johnston-Cox, H., Weng, Y. H. & Hermann, T. Functional architecture of HCV IRES domain II stabilized by divalent metal ions in the crystal and in solution. Angew Chem Int Ed Engl 46, 226-9 (2007).). RNA constructs containing the subdomain IIa of the HCV IRES, with A54 replaced by 2AP, were used in titrations with the RNA-binding ligands. In a typical titration ligand was added starting at 1 nM concentration, going to 1 mM concentration in 20 to 30 addition steps, and 2AP fluorescence recorded after each addition. Fluorescence measurements were performed on a thermostatted RF-5301PC spectrofluorometer (Shimadzu, Columbia, Md.) at 25° C. Emission spectra of 2AP-labelled RNA were recorded in 10 mM sodium cacodylate buffer, pH 6.5, at 0.5 μM RNA concentration and while irradiating at 310 nm. Apparent dissociation constants ($EC_{50}$) of ligands were calculated with the Sigmaplot software (Systat Software, Point Richmont, Calif.) by fitting dose-response binding curves to the relative fluorescence intensity plotted vs. the logarithm(10) of the titrant concentration (see FIG. 1 in [0157]). Raw fluorescence data were normalized by division by the total fluorescence change over the titrations. FIG. 1A shows the results of the fluorescence affinity assays on MC060A HCV replicon assays were used to measure compound activity in cells. The impact of compounds on HCV replicon replication was assessed, using a method that was previously described (ref.: Wyles, D. L., Kaihara, K. A., Vaida, F. & Schooley, R. T. Synergy of small molecular inhibitors of hepatitis C virus replication directed at multiple viral targets. J Virol 81, 3005-8 (2007).) in cells stably expressing the BM4-5 FEO replicon in 96-well plates (10,000 cells/well). Generation of the BM4-5 FEO RNA (genotype 1b HCV) replicon from the corresponding DNA plasmid using T7 RNA polymerase (Mega-script, Ambion) was previously described (ref.: Wyles et al., see citation above). For testing the effect of compounds on the HCV replicon cells were incubated with compound for 48 hours and the results expressed as the mean (±SEM) of the relative light units for each condition. A sigmoidal dose response curve was then fitted to the data using Prism4.0 (GraphPad Software). FIGS. 1B, 7A, 8A, and 9A show the results of the replicon assays for MC069A, compound S3, compound K3 and compound T3, respectively.

Cytotoxicity assays were used to measure compound toxicity in cells. Cytotoxicity was assessed using a standard colorimetric cell viability assay at concentrations of compound 2 up to 50 µM ( ). FIGS. 1C, 7B, 8B, and 9B show the results of the cytotoxicity assays for CellTiter 96 AQ, Promega MC069A, compound S3, compound K3 and compound T3, respectively.

Pharmaceutical Compositions

In another aspect, the present application relates to a pharmaceutical composition comprising a compound of Formula I or Formula II as described above or pharmaceutically acceptable salts thereof, and a physiologically acceptable carrier, diluent, or excipient, or a combination thereof.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, intramuscular, intraocular, intranasal, intravenous, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical compositions can generally be tailored to the specific intended route of administration.

The term "physiologically acceptable" or "pharmaceutically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990, which is hereby incorporated by reference in its entirety.

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

Alternately, one may administer the compound in a local rather than systemic manner, for example, via injection of the compound directly into the desired area, often in a depot or sustained release formulation. Furthermore, one may administer the drug in a targeted drug delivery system, for example, in a liposome coated with a tissue-specific antibody. The liposomes can be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes.

Pharmaceutical compositions for use in accordance with the present disclosure thus may be formulated in conventional manner using one or more physiologically acceptable carriers comprising excipients and auxiliaries, which facilitate processing of the active compounds into preparations, which can be used pharmaceutically. Proper formulation is dependent upon the route of administration chosen. Any of the well-known techniques, carriers, and excipients may be used as suitable and as understood in the art; e.g., as disclosed in Remington's Pharmaceutical Sciences, cited above.

For injection, the agents disclosed herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds disclosed herein to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipient with pharmaceutical combination disclosed herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present disclosure are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In some embodiments, a co-solvent system may be used to prepare the pharmaceutical compositions. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80™; the fraction size of polyethylene glycol may be varied; and other biocompatible polymers may replace polyethylene glycol, e.g., polyvinyl pyrrolidone. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the compounds used in the pharmaceutical combinations disclosed herein may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free acids or base forms.

Pharmaceutical compositions suitable for use in the methods disclosed herein include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

The exact formulation, route of administration and dosage for the pharmaceutical compositions disclosed herein can be chosen by the individual physician in view of the patient's condition. (See e.g., Fingl et al. 1975, in "The Pharmacological Basis of Therapeutics", Chapter 1, which is hereby incorporated by reference in its entirety). Typically, the dose range of the composition administered to the patient can be from about 0.5 to 1000 mg/kg of the patient's body weight, or 1 to 500 mg/kg, or 10 to 500 mg/kg, or 50 to 100 mg/kg of the patient's body weight. The dosage may be a single one or a series of two or more given in the course of one or more days, as is needed by the patient. Where no human dosage is established, a suitable human dosage can be inferred from $ED_{50}$ or $ID_{50}$ values, or other appropriate values derived from in vitro or in vivo studies, as qualified by toxicity studies and efficacy studies in animals.

Although the exact dosage can be determined on a drug-by-drug basis, in most cases, some generalizations regarding the dosage can be made. The daily dosage regimen for an adult human patient may be, for example, an oral dose of between 0.1 mg and 500 mg of each ingredient, preferably between 1 mg and 250 mg, e.g. 5 to 200 mg or an intravenous, subcutaneous, or intramuscular dose of each ingredient between 0.01 mg and 100 mg, preferably between 0.1 mg and 60 mg, e.g. 1 to 40 mg of each ingredient of the pharmaceutical compositions disclosed herein or a pharmaceutically acceptable salt thereof calculated as the free base, the composition being administered 1 to 4 times per day. Alternatively the compositions disclosed herein may be administered by continuous intravenous infusion, preferably at a dose of each ingredient up to 400 mg per day. Thus, the total daily dosage by oral administration of each ingredient will typically be in the range 1 to 2000 mg and the total daily dosage by parenteral administration will typically be in the range 0.1 to 400 mg. In some embodiments, the compounds can be administered for a period of continuous therapy, for example for a week or more, or for months or years.

Dosage amount and interval may be adjusted individually to provide plasma levels of the active moiety, which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen, which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound disclosed herein formulated in a compatible pharmaceutical carrier may also be prepared, placed in an appropriate container, and labeled for treatment of an indicated condition.

EXAMPLES

Example 1

Synthesis of Compound MC069A

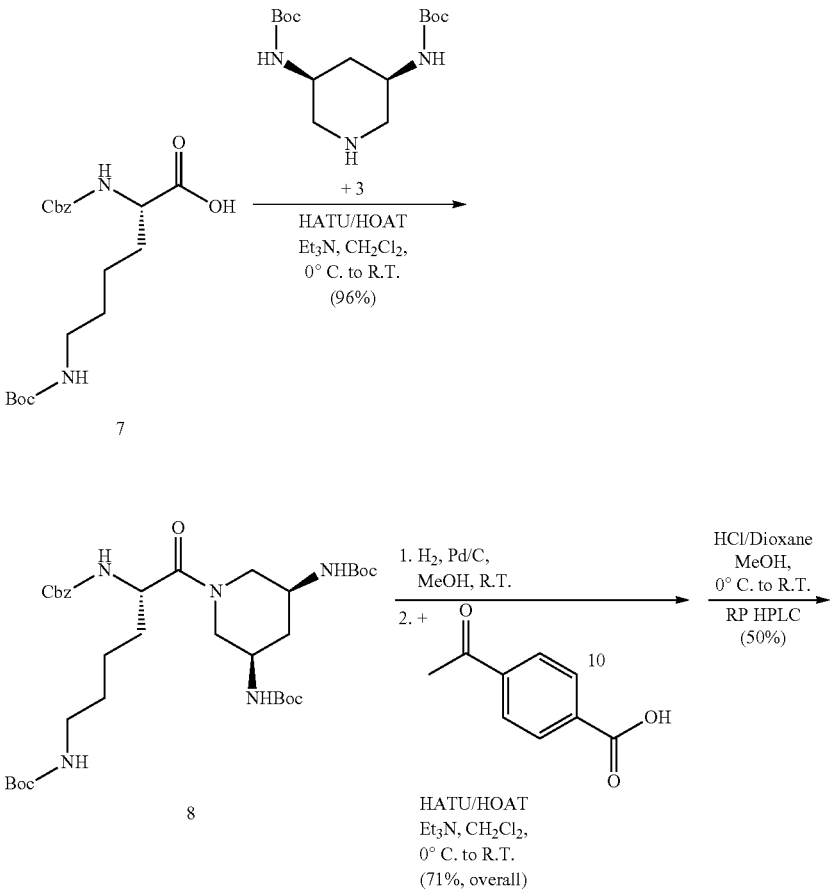

-continued

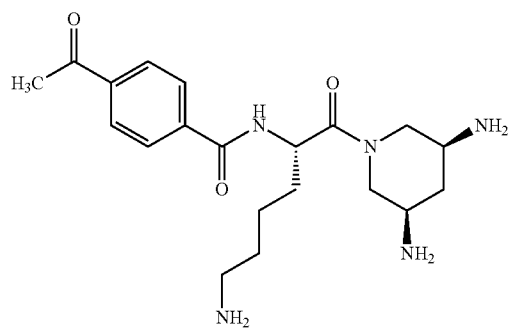

MC069A (HATU = 2-(7-Aza-1H-benzotriazole-1-yl)-1, 1, 3, 3-tetramethyluronium salt, HOAt = 1-Hydroxy-7-azabenzotriazole)

To a solution of N-Cbz-Lys(Boc) (7) (1 eq) and 3,5-diaminopiperidine(Boc)₂ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO₃ and once with saturated NaCl. The combined organic layers were dried over Na₂SO₄ and the solvent was removed under reduced pressure. The crude product 8 was purified by silica gel chromatography, using 2% (v/v) methanol (MeOH)/dichloromethane (DCM).

The pure compound (8) was dissolved in anhydrous methanol (0.1 M) and the solution was flushed with argon. Following slow addition of Pd on carbon catalyst (Pd/C, 10% by weight), the solution was purged twice with hydrogen gas, using a hydrogen balloon. The third balloon was left for the reaction to stir at room temperature for 16-24 hrs. The reaction mixture was filtered over a pad of celite and the solvent was removed under reduced pressure. The crude product was purified by silica gel column chromatography starting at 2% (v/v) MeOH/DCM and ending at 6% MeOH/DCM, with increments of 1%.

To a solution of H-Lys(Boc)-DAP(Boc)₂ (1 eq.) and 4-acetylbenzoic acid (10) (1 eq.) in dichloromethane (0.05M), triethylamine (7 eq.) was added, followed by HATU (1.1 eq.) and HOAT (1.2 eq.), while stirring under argon at 0° C. The reaction mixture was stirred for 3.5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO₃ and once with saturated NaCl. The combined organic layers were dried over Na₂SO₄ and the solvent was removed under reduced pressure. The crude product was purified by silica gel chromatography, starting at 2% (v/v) MeOH/DCM and continuing at 3% MeOH/DCM.

The product of the previous coupling reaction was dissolved (0.02M) in a mixture of anhydrous methanol (2 parts) and 4M HCl/dioxane (1 part), while stirring under argon at 0° C. The reaction mixture was stirred for 3-5 hours and the temperature was let equilibrate to room temperature. The reaction mixture was diluted threefold with toluene and the solvent was removed under reduced pressure. The process of adding toluene and evaporating was repeated twice.

Figure 2A:
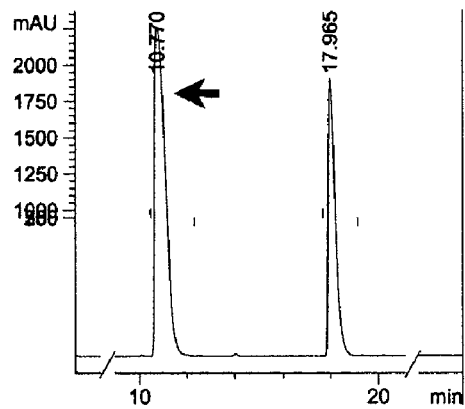
FIG. 2A is an elution profile of MC069A on C18 HPLC column. The compound peak at 10.88 min is marked by a peak.
Figure 2B:
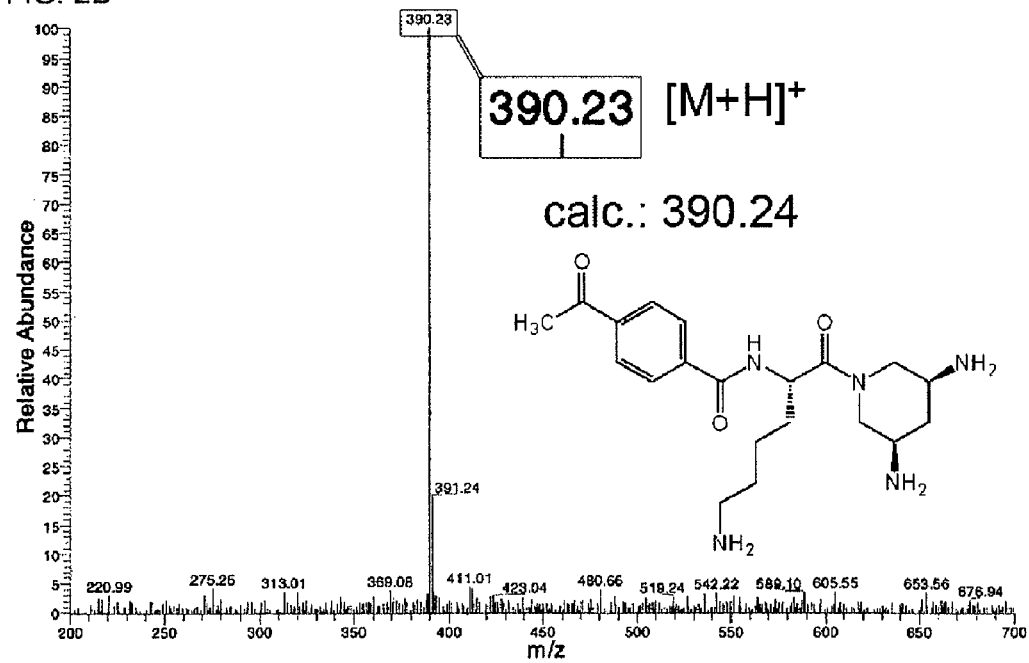
FIG. 2B is a Mass-spectrometric analysis of MC069A purified by reverse phase HPLC.

The crude compound (50 mg) was dissolved in deionized water (1 mL) and sonicated for ten minutes. The solution was filtered and centrifuged. The solution was injected multiple times (99 µL maximum) into a C18 semi preparative HPLC column. The elution was monitored by UV Vis, at $\lambda=205$ nm, $\lambda=220$ nm and $\lambda=257$ nm (elution gradient: 5-30% H₂0/ACN, 0.1% TFA, in 25 minutes). The peaks containing the product from the several injections were combined and the solvent was removed by lyophilization, yielding a white flaky solid. The compound was characterized by NMR and mass-spectrometry (FIG. 2B).

Example 2

Synthesis of Compounds K2-5

Figure 3:
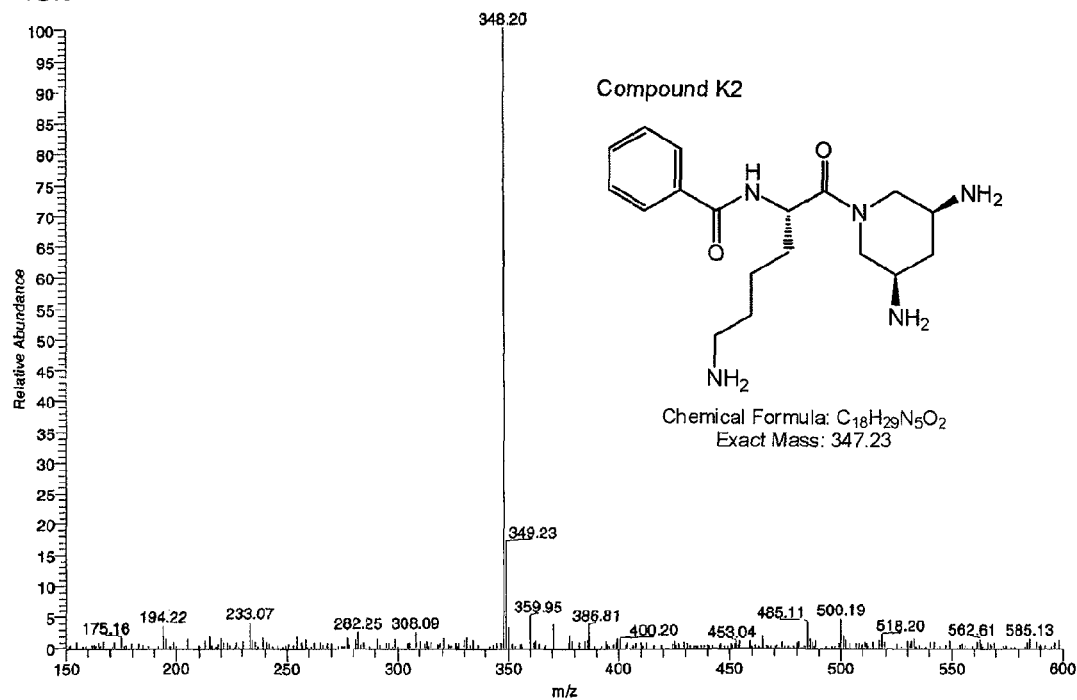
FIG. 3 is a Mass-spectrometric analysis of compound K2 purified by reverse phase HPLC.

The synthetic procedures to produce compound K2 generally follow the procedures outlined in Example 1. In the synthesis of compound K2, 4-acetylbenzoic acid is replaced by benzoic acid. The compound was characterized by NMR and mass-spectrometry (FIG. 3A). In the synthesis of compound K3, 4-acetylbenzoic acid is replaced by mandelic acid. In the synthesis of compound K4, 4-acetylbenzoic acid is replaced by lactic acid. In the synthesis of compound K5,4-acetylbenzoic acid is replaced by 4-hydroxylbenzoic acid.

Example 3

Synthesis of Compound K6

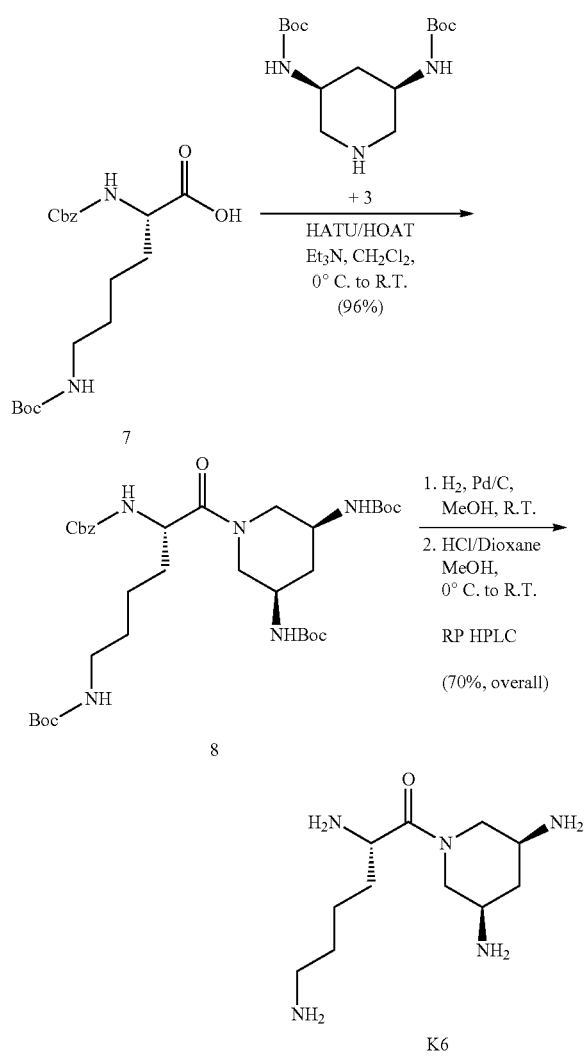

To a solution of N-Cbz-Lys(Boc) (7) (1 eq) and 3,5-diaminopiperidine(Boc)$_2$ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO$_3$ and once with saturated NaCl. The combined organic layers were dried over Na$_2$SO$_4$ and the solvent was removed under reduced pressure. The crude product 8 was purified by silica gel chromatography, using 2% (v/v) methanol (MeOH)/dichloromethane (DCM).

The intermediate H-Lys(Boc)-DAP(Boc)$_2$ (8) was dissolved in anhydrous methanol (0.1 M) and the solution was flushed with argon. Following slow addition of Pd on carbon catalyst (Pd/C 10% by weight), the solution was purged twice with hydrogen gas, using a hydrogen balloon. The third balloon was left for the reaction to stir at room temperature for 24 hrs. The reaction mixture was then filtered over a pad of celite to remove the catalyst. To the methanol solution 4M HCl/dioxane were added (1 eq.), while stirring under argon at 0° C. The reaction mixture was stirred for 4 hours and the temperature was let equilibrate to room temperature. The reaction mixture was then diluted threefold with toluene and the solvent was removed under reduced pressure. The process of adding toluene and evaporating was repeated twice. Finally, the crude compound was dissolved in deionized water.

The crude compound (50 mg) was dissolved in deionized water (1 mL) and sonicated for ten minutes. The solution was filtered and centrifuged. The solution was injected multiple times (99 μL maximum) into a C18 semi preparative HPLC column. The elution was monitored by UV Vis, at λ=205 nm, λ=220 nm and λ=257 nm (elution gradient: 5-30% H$_2$O/ACN, 0.1% TFA, in 25 minutes). The peaks containing the product from the several injections were combined and the solvent was removed by lyophilization, yielding a white flaky solid. The compound was characterized by NMR and mass-spectrometry.

Example 4

Synthesis of Compounds R1 and R2

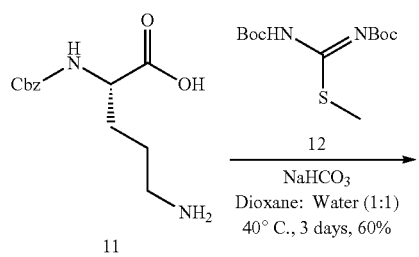

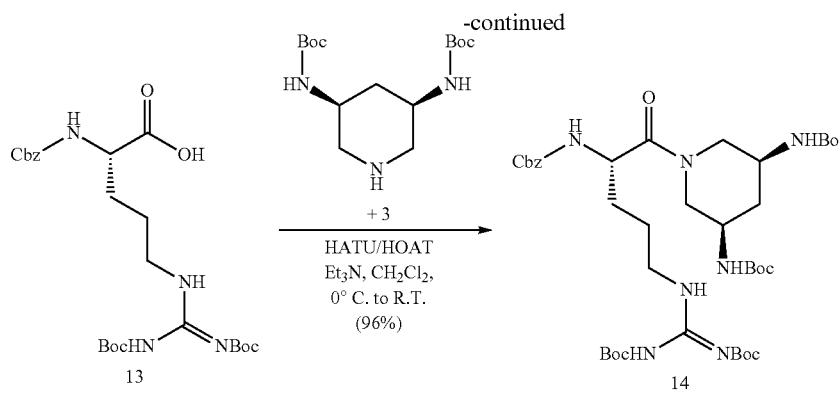
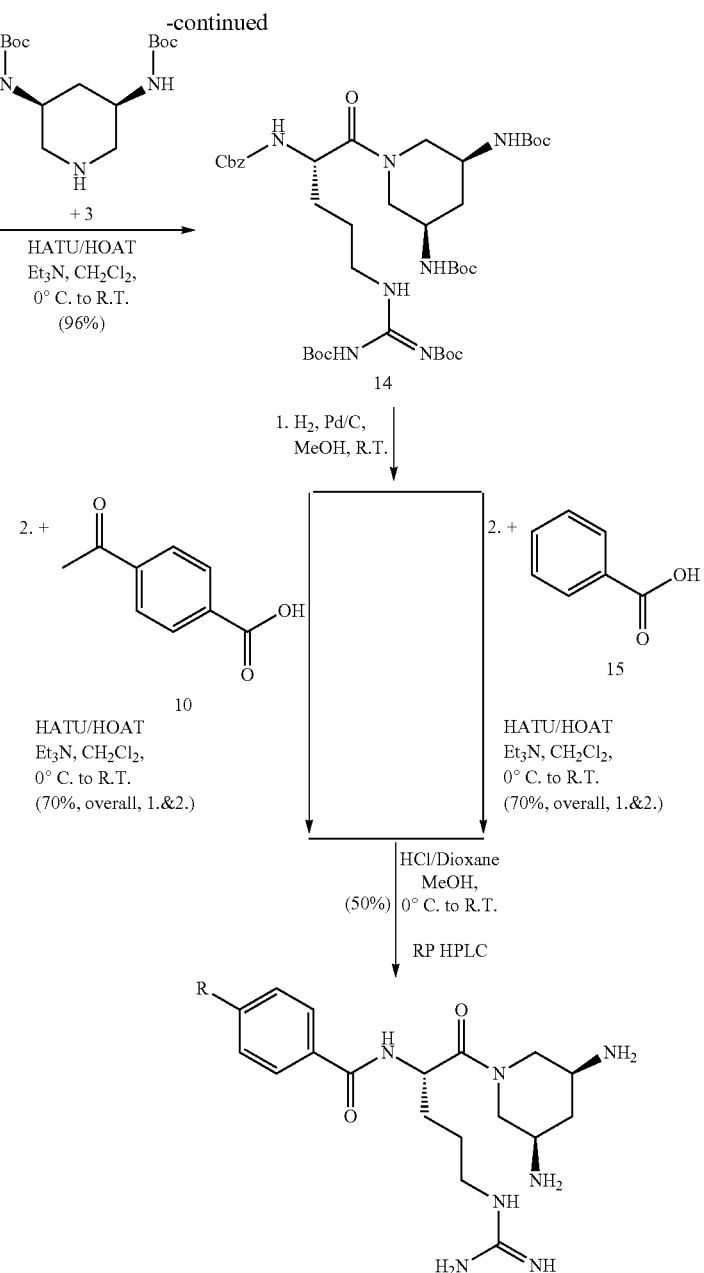

Compound R1 (R = CH₃—C(=O)—)
Compound R2 (R = H)
(HATU = 2-(7-Aza-1H-benzotriazole-1-yl)-1,1,3,3-tetramethyluronium salt, HOAt = 1-Hydroxy-7-azabenzotriazole)

To a solution of NaHCO₃ (1.18 eq.) in dioxane:water, N-Cbz-ornithine(Boc)-OH (11) (1 eq., Concentration=0.16M) was added, then N,N'-Boc₂-S-methylisothiourea (12) (0.75 eq.), while stirring under argon. The reaction was stirred at 40° C. for 3 days, after which the solvent was removed under reduced pressure. The crude was diluted with ethyl acetate and washed twice with 0.3M HCl and once with saturated NaCl. The combined organic layers were dried over Na₂SO₄ and the solvent was removed under reduced pressure. The crude product was purified by silica gel chromatography, using 2% (v/v) methanol (MeOH)/dichloromethane (DCM).

To a solution of Cbz/Boc protected (S)-arginine) (12) (1 eq) and 3,5-diaminopiperidine(Boc)₂ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO₃ and once with saturated NaCl. The combined organic layers were dried over Na₂SO₄ and the solvent was removed under reduced pressure. The crude product 14 was purified by silica gel chromatography, using 2% (v/v) methanol (MeOH)/dichloromethane (DCM).

The pure compound (14) was dissolved in anhydrous methanol (0.1 M) and the solution was flushed with argon. Following slow addition of Pd on carbon catalyst (Pd/C, 10% by weight), the solution was purged twice with hydrogen gas, using a hydrogen balloon. The third balloon was left for the reaction to stir at room temperature for 16-24 hrs. The reaction mixture was filtered over a pad of celite and the solvent was removed under reduced pressure. The crude product was purified by silica gel column chromatography starting at 2% (v/v) MeOH/DCM and ending at 6% MeOH/DCM, with increments of 1%.

To a solution of H-Lys(Boc)-DAP(Boc)$_2$ (1 eq.) and 4-acetylbenzoic acid (10) (1 eq.) in dichloromethane (0.05M), triethylamine (7 eq.) was added, followed by HATU (1.1 eq.) and HOAT (1.2 eq.), while stirring under argon at 0° C. for the synthesis of R1. To a solution of H-Lys(Boc)-DAP (Boc)$_2$ (1 eq.) and benzoic acid (15) (1 eq.) in dichloromethane (0.05M), triethylamine (7 eq.) was added, followed by HATU (1.1 eq.) and HOAT (1.2 eq.), while stirring under argon at 0° C. for the synthesis of compound R2. In each case, the reaction mixture was stirred for 3.5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO$_3$ and once with saturated NaCl. The combined organic layers were dried over Na$_2$SO$_4$ and the solvent was removed under reduced pressure. The crude product was purified by silica gel chromatography, starting at 2% (v/v) MeOH/DCM and continuing at 3% MeOH/DCM.

The product of the previous coupling reaction was dissolved (0.02M) in a mixture of anhydrous methanol (2 parts) and 4M HCl/dioxane (1 part), while stirring under argon at 0° C. The reaction mixture was stirred for 3-5 hours and the temperature was let equilibrate to room temperature. The reaction mixture was diluted threefold with toluene and the solvent was removed under reduced pressure. The process of adding toluene and evaporating was repeated twice.

Figure 4A:
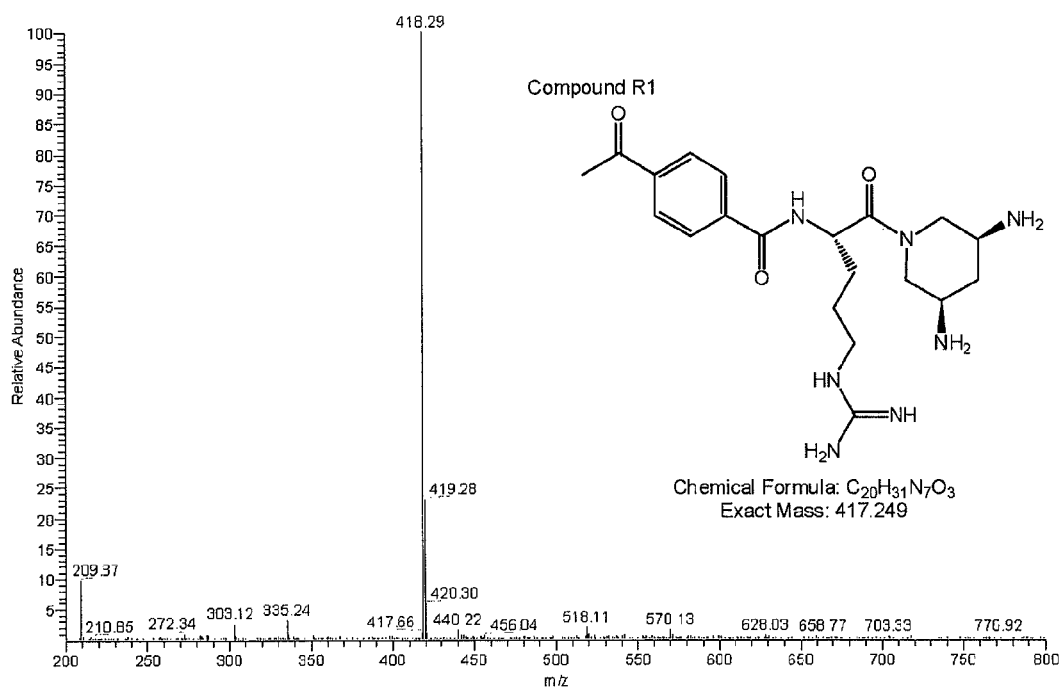
FIG. 4A is a Mass-spectrometric analysis of compound R1 purified by reverse phase HPLC.
Figure 4B:
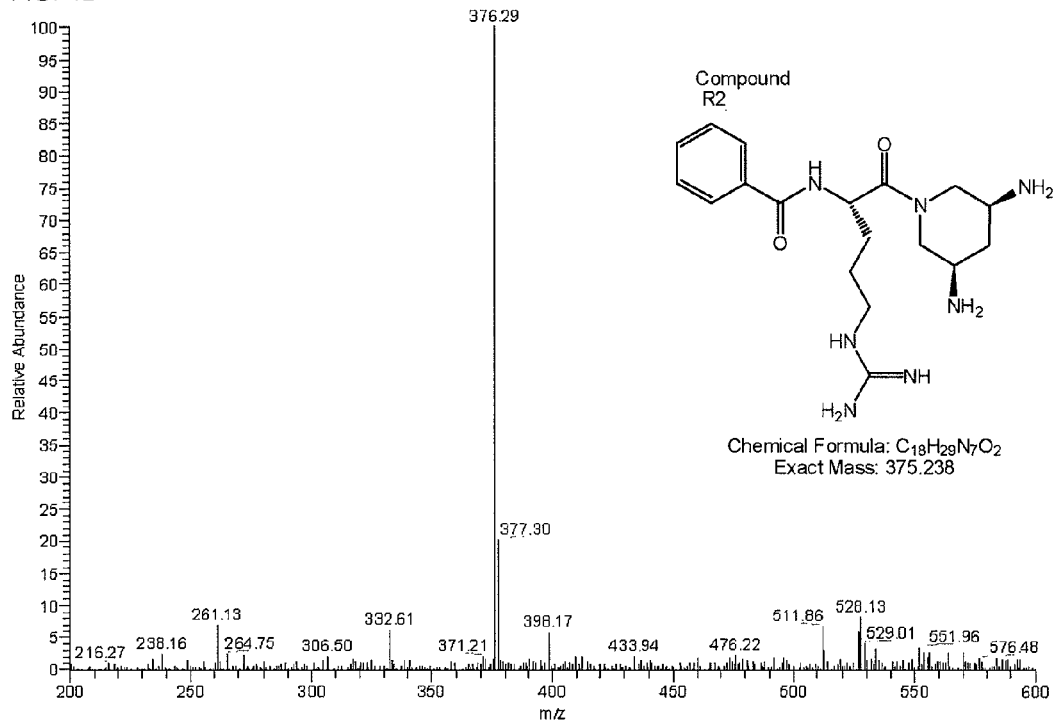
FIG. 4B is a Mass-spectrometric analysis of compound R2 purified by reverse phase HPLC.
Figure 5:
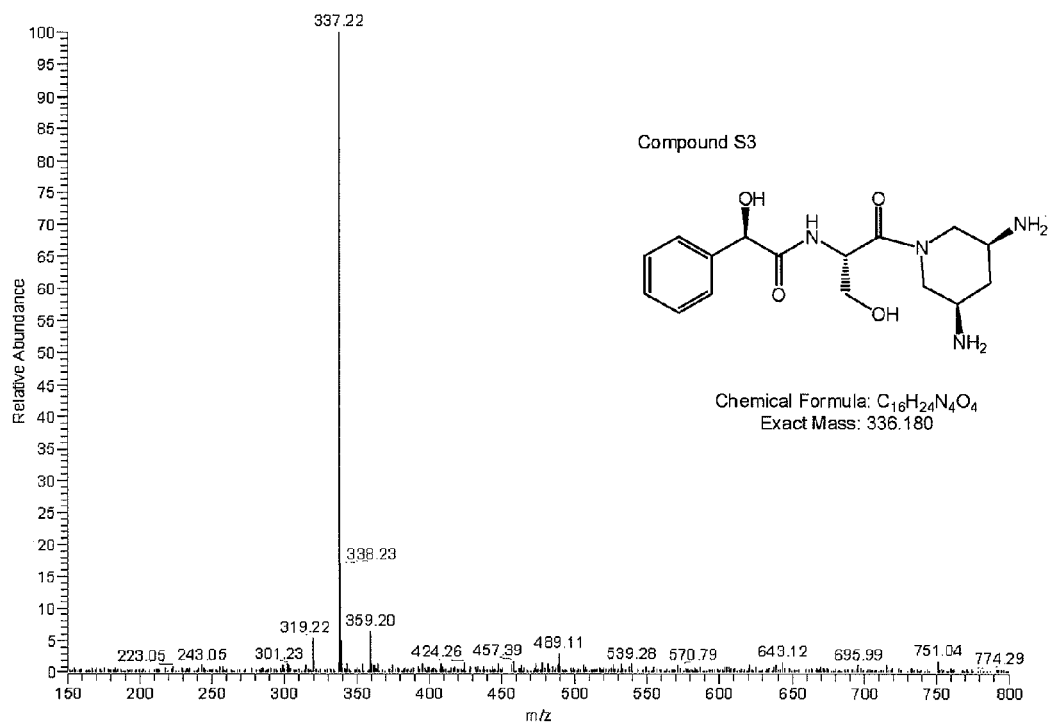
FIG. 5 is a Mass-spectrometric analysis of compound S3 purified by reverse phase HPLC.
Figure 6:
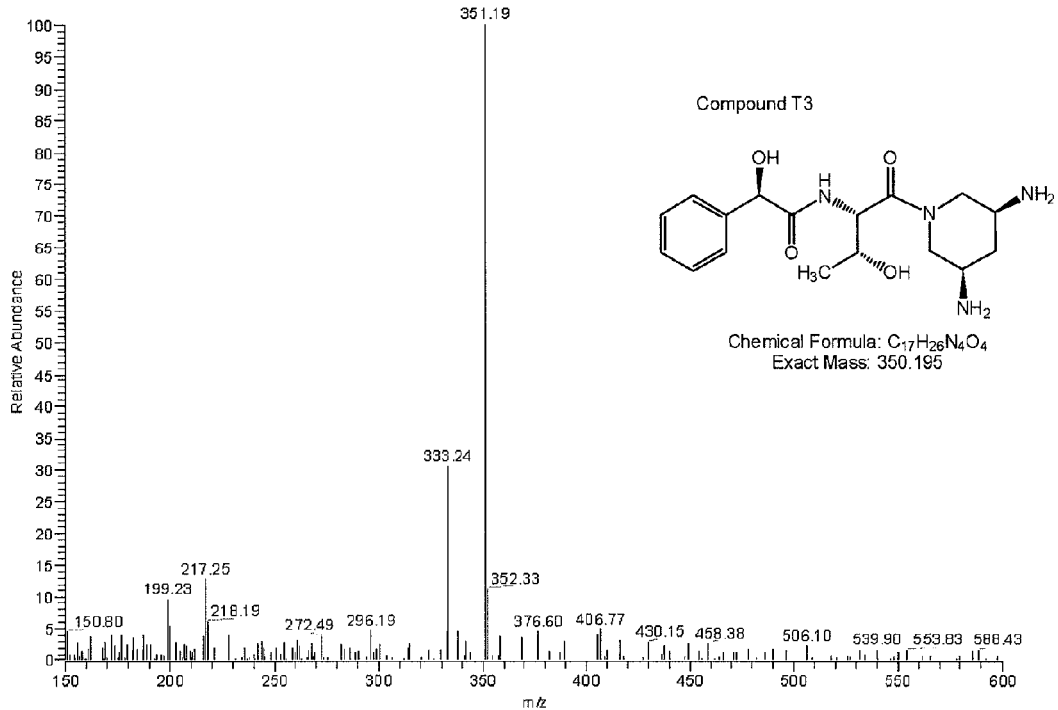
FIG. 6 is a Mass-spectrometric analysis of compound T3 purified by reverse phase HPLC.
Figure 7A:
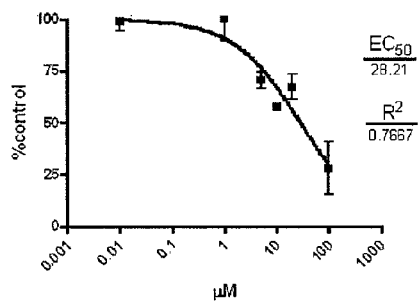
FIG. 7A is a diagram showing inhibition of HCV by compound S3 in a subgenomic replicon.
Figure 7B:
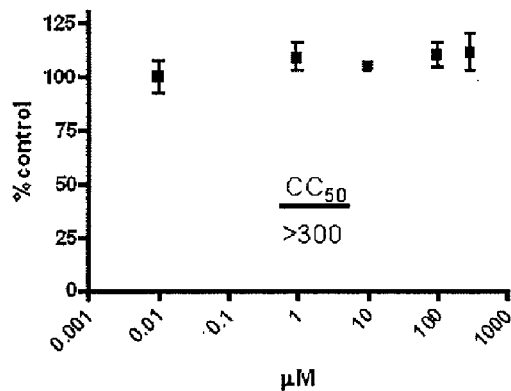
FIG. 7B is a diagram showing inhibition of HCV by compound S3 in a cytotoxicity assay.
Figure 8A:
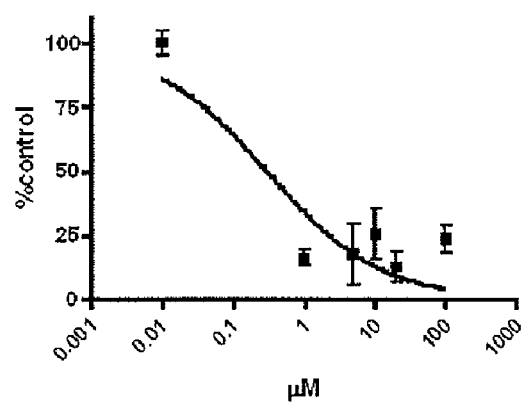
FIG. 8A is a diagram showing inhibition of HCV by compound K3 in a subgenomic replicon.
Figure 8B:
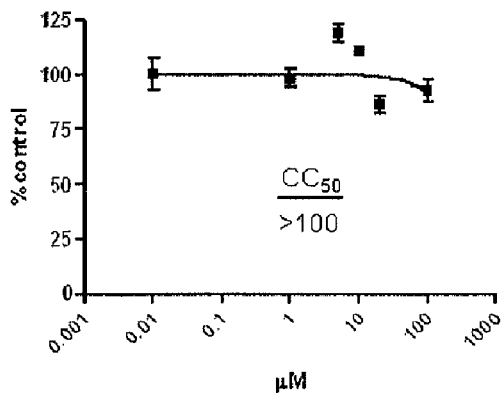
FIG. 8B is a diagram showing inhibition of HCV by compound K3 in a cytotoxicity.
Figure 9A:
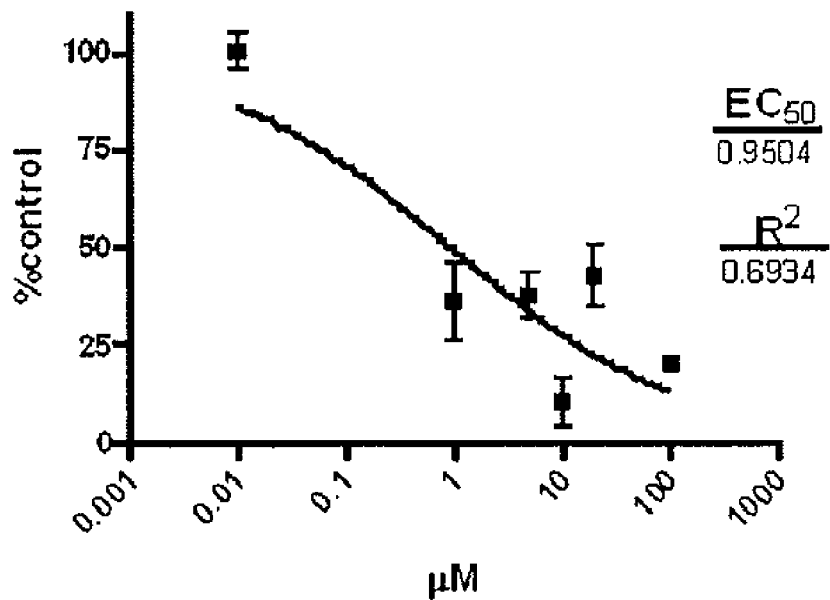
FIG. 9A is a diagram showing inhibition of HCV by compound T3 in a subgenomic replicon.
Figure 9B:
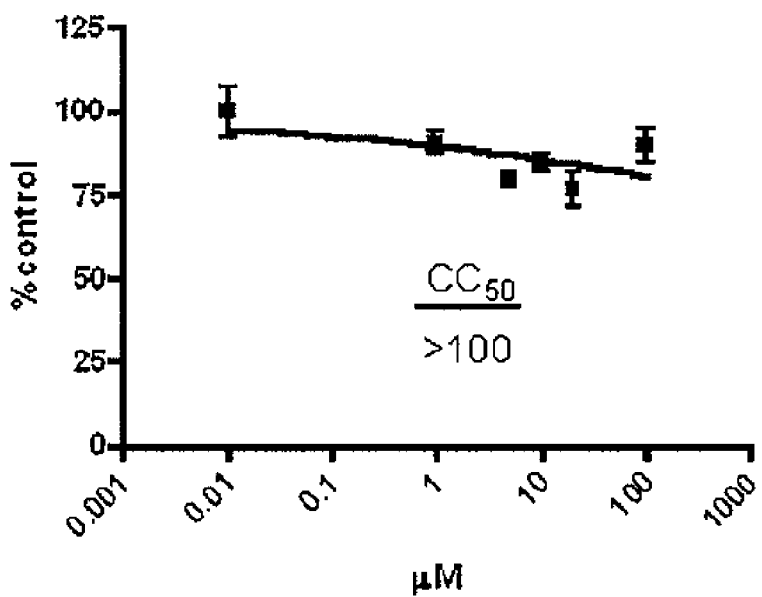
FIG. 9B is a diagram showing inhibition of HCV by compound T3 in a cytotoxicity assay.

The crude compound (50 mg) was dissolved in deionized water (1 mL) and sonicated for ten minutes. The solution was filtered and centrifuged. The solution was injected multiple times (99 μL maximum) into a C18 semi preparative HPLC column. The elution was monitored by UV Vis, at λ=205 nm, λ=220 nm and λ=257 nm (elution gradient: 5-30% H$_2$O/ACN, 0.1% TFA, in 25 minutes). The peaks containing the product from the several injections were combined and the solvent was removed by lyophilization, yielding a white flaky solid. The compounds were characterized by NMR and mass-spectrometry (FIGS. 4A and 4B).

Example 5

Synthesis of Compounds R3-R5

The synthetic procedures to produce compounds R3, R4, and R5 generally follow the procedures outlined in Example 7. In the synthesis of compound K3, 4-acetylbenzoic acid (10) is replaced by mandelic acid. In the synthesis of compound K4, 4-acetylbenzoic acid (10) is replaced by lactic acid. In the synthesis of compound K5, 4-acetylbenzoic acid (10) is replaced by 4-hydroxylbenzoic acid.

Example 6

Synthesis of Compound R6

To a solution of NaHCO$_3$ (1.18 eq.) in dioxane:water, N-Cbz-ornithine(Boc)-OH (11) (1 eq., Concentration=0.16M) is added, then N,N'-Boc$_2$-S-methylisothiourea (12) (0.75 eq.), while stirring under argon. The reaction is stirred at 40° C. for 3 days, after which the solvent is removed under reduced pressure. The crude is diluted with ethyl acetate and ished twice with 0.3M HCl and once with saturated NaCl. The combined organic layers were dried over Na$_2$SO$_4$ and the solvent is removed under reduced pressure. The crude product is purified by silica gel chromatography, using 2% (v/v) methanol (MeOH)/dichloromethane (DCM).

To a solution of Cbz/Boc protected (S)-arginine) (12) (1 eq) and 3,5-diaminopiperidine(Boc)$_2$ (3) (1 eq.) in dichloromethane (0.1 M), triethylamine (7 eq.) is added, followed by HATU (1.1 eq.) and HOAT (1.2 eq.), while stirring under argon at 0° C. The reaction mixture is stirred for 5 hours and the temperature is let equilibrate to room temperature. The reaction progress is monitored by TLC. Upon complete consumption of starting material, the reaction mixture is diluted with dichloromethane and washed once with 0.1 M HCl, once with saturated NaHCO$_3$ and once with saturated NaCl. The combined organic layers were dried over Na$_2$SO$_4$ and the solvent is removed under reduced pressure. The crude product 14 is purified by silica gel chromatography, using 2% (v/v) methanol (MeOH)/dichloromethane (DCM).

The pure compound (14) is dissolved in anhydrous methanol (0.1 M) and the solution is flushed with argon. Following slow addition of Pd on carbon catalyst (Pd/C 10% by weight), the solution is purged twice with hydrogen gas, using a hydrogen balloon. The third balloon is left for the reaction to stir at room temperature for 24 hrs. The reaction mixture is then filtered over a pad of celite to remove the catalyst. To the methanol solution 4M HCl/dioxane were added (1 eq.), while stirring under argon at 0° C. The reaction mixture is stirred for 4 hours and the temperature is let equilibrate to room temperature. The reaction mixture is then diluted threefold with toluene and the solvent is removed under reduced pressure. The process of adding toluene and evaporating is repeated twice. Finally, the crude compound is dissolved in deionized water.

The crude compound (50 mg) is dissolved in deionized water (1 mL) and sonicated for ten minutes. The solution is filtered and centrifuged. The solution is injected multiple times (99 μL maximum) into a C18 semi preparative HPLC column. The elution is monitored by UV Vis, at λ=205 nm, λ=220 nm and λ=257 nm (elution gradient: 5-30% H$_2$O/ACN, 0.1% TFA, in 25 minutes). The peaks containing the product from the several injections were combined and the solvent is removed by lyophilization, yielding a white flaky solid. The compound is characterized by NMR and mass-spectrometry.

Example 7

Synthesis of Compound S1, S2, S3

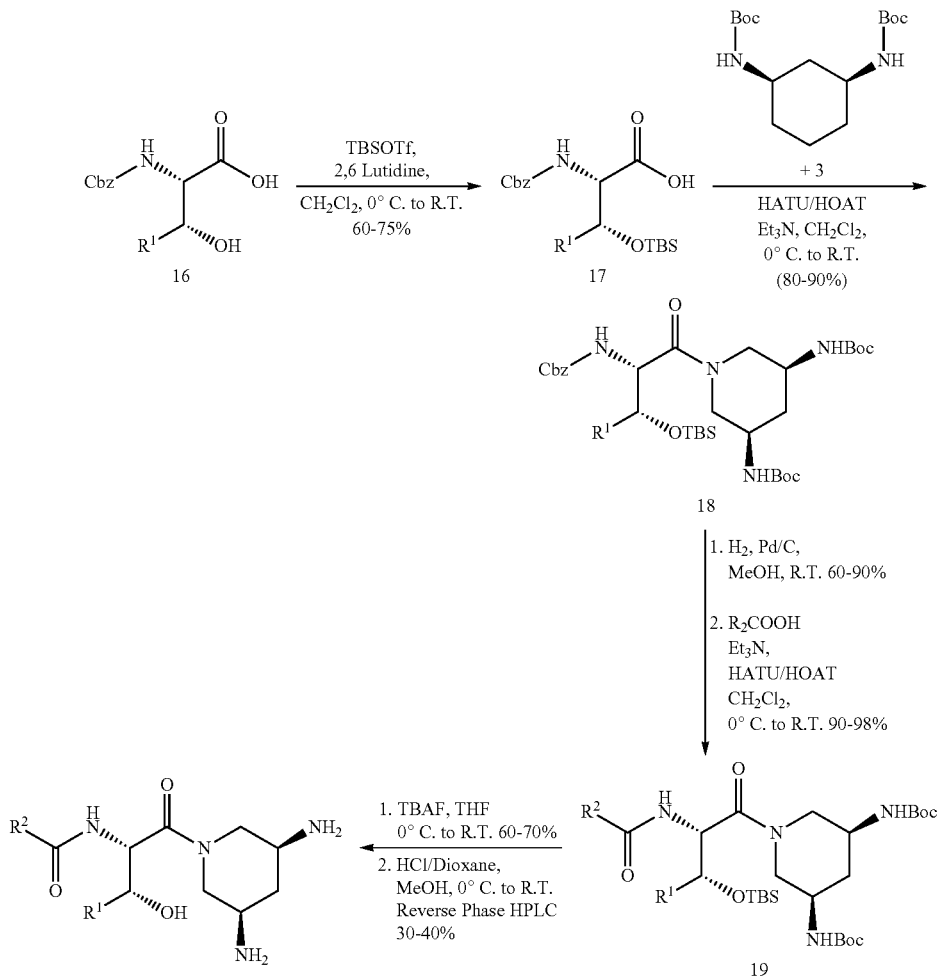

Compound S1 ($R^1$ = H, $R^2$ = 4-$CH_3C(=O)$—Ph—)
Compound S2 ($R^1$ = H, $R^2$ = Ph—)
Compound S3 ($R^1$ = H, $R^2$ = Ph—CH(—OH)—)

To a solution of N—CBZ-Ser-OH($R_1$=H) in $CH_2Cl_2$ (Concentration=0.3M), 2,6-Lutidine was added (1.3 eq.), then tert-Butyldimethylsilyl trifluoromethanesulfonate (TB-DMSOTf) (3 eq.), while stirring under argon at 0° C. The reaction was stirred for 4 hours and the temperature was let spontaneously rise to room temperature. The crude was washed twice with 5% aq. citric acid, and once with saturated NaCl. The combined organic layers were dried with $Na_2SO_4$, and the solvent evaporated under reduced pressure. The crude was purified by silica gel column chromatography using 5% Methanol/Dichloromethane.

To a solution of intermediate (17) and 3,5-diaminopiperidine(Boc)$_2$ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated $NaHCO_3$ and once with saturated NaCl. The combined organic layers were dried over $Na_2SO_4$ and the solvent was removed under reduced pressure. The crude product 18 was purified by silica gel chromatography, using 2% (v/v) methanol (MeOH)/dichloromethane (DCM).

The pure compound (18) was dissolved in anhydrous methanol (0.1 M) and the solution was flushed with argon. Following slow addition of Pd on carbon catalyst (Pd/C, 10% by weight), the solution was purged twice with hydrogen gas, using a hydrogen balloon. The third balloon was left for the reaction to stir at room temperature for 16-24 hrs. The reaction mixture was filtered over a pad of celite and the solvent was removed under reduced pressure. The crude product was purified by silica gel column chromatography starting at 2% (v/v) MeOH/DCM and ending at 6% MeOH/DCM, with increments of 1%.

To a solution of intermediate 18 and 4-acetylbenzoic acid (1 eq.) in dichloromethane (0.05M), triethylamine (7 eq.) was added, followed by HATU (1.1 eq.) and HOAT (1.2 eq.), while stirring under argon at 0° C. for the synthesis of compound S1. To a solution of intermediate 18 and benzoic acid (1 eq.) in dichloromethane (0.05M), triethylamine (7 eq.) was added, followed by HATU (1.1 eq.) and HOAT (1.2 eq.), while stirring under argon at 0° C. for the synthesis of compound S2. To a solution of intermediate 18 and lactic acid (1 eq.) in dichloromethane (0.05M), triethylamine (7 eq.) was added, followed by HATU (1.1 eq.) and HOAT (1.2 eq.), while stirring under argon at 0° C. for the synthesis of compound S3. For each compound, the reaction mixture was stirred for 3.5 hours and the temperature was let equilibrate to room temperature. The reaction progress was monitored by TLC. Upon complete consumption of starting material, the reaction mixture was diluted with dichloromethane and washed once with 0.1 M HCl, once with saturated $NaHCO_3$ and once with saturated NaCl. The combined organic layers were dried over $Na_2SO_4$ and the solvent was removed under reduced pressure. The crude product was purified by silica gel chromatography, starting at 2% (v/v) MeOH/DCM and continuing at 3% MeOH/DCM.

To a solution of intermediate 19 in THF (Concentration=0.05M), a solution of tert-butylammonium fluoride (TBAF) was added (3 eq. of TBAF), while stirring under argon at 0° C. The reaction was stirred for 4 hours and the temperature was let equilibrate to room temperature. The reaction mixture was diluted with ethyl acetate, washed twice with $H_2O$ and once with saturated NaCl. The combined organic layers were dried with $Na_2SO_4$, and the solvent evaporated under reduced pressure. The crude was purified by silica gel column chromatography using 7.5% Methanol/Dichloromethane.

The product of the previous coupling reaction was dissolved (0.02M) in a mixture of anhydrous methanol (2 parts) and 4M HCl/dioxane (1 part), while stirring under argon at 0° C. The reaction mixture was stirred for 3-5 hours and the temperature was let equilibrate to room temperature. The reaction mixture was diluted threefold with toluene and the solvent was removed under reduced pressure. The process of adding toluene and evaporating was repeated twice.

The crude compound (50 mg) was dissolved in deionized water (1 mL) and sonicated for ten minutes. The solution was filtered and centrifuged. The solution was injected multiple times (99 μL maximum) into a C18 semi preparative HPLC column. The elution was monitored by UV Vis, at λ=205 nm, λ=220 nm and λ=257 nm (elution gradient: 5-30% $H_2O$/ACN, 0.1% TFA, in 25 minutes). The peaks containing the product from the several injections were combined and the solvent was removed by lyophilization, yielding a white flaky solid. The compound was characterized by NMR and mass-spectrometry.

Example 8

Synthesis of Compound S4 and S5

The synthetic procedures to produce compounds S4 and S5 generally follow the procedures outlined in Example 7. In the synthesis of compound S4, 4-acetylbenzoic acid is replaced by lactic acid. In the synthesis of compound S5, 4-acetylbenzoic acid is replaced by 4-hydroxylbenzoic acid.

Example 9

Synthesis of Compound T1, T2, T3

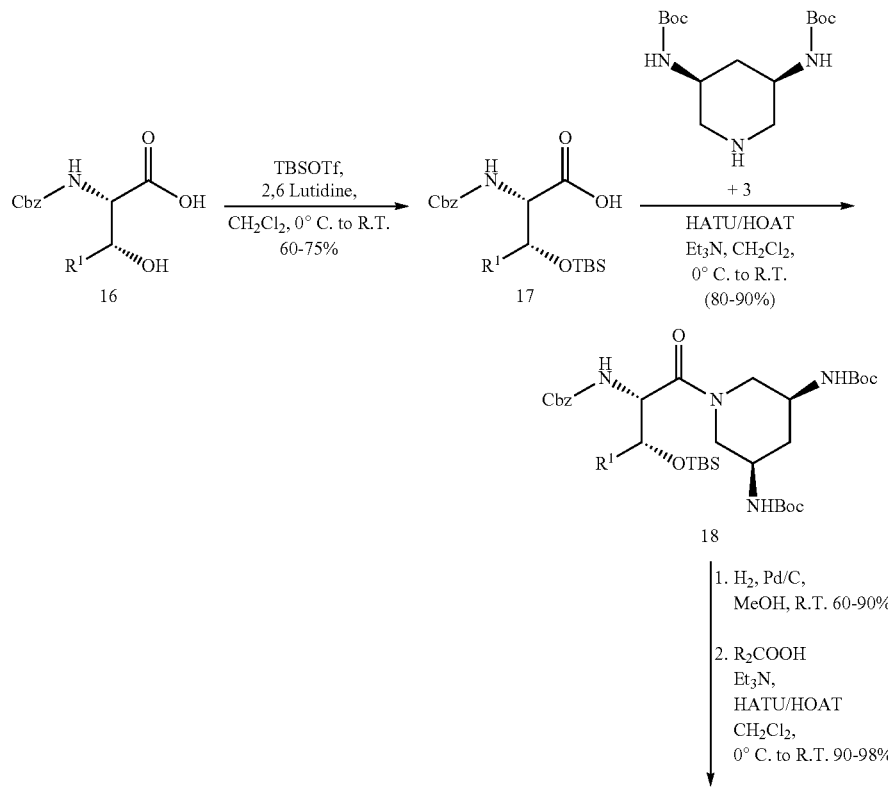

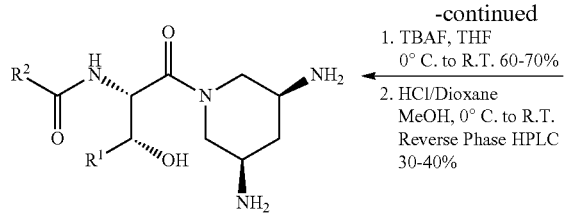 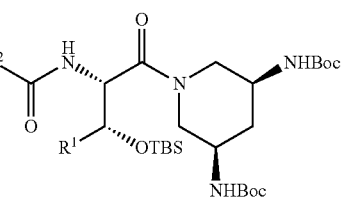

19

Compound T1 (R¹ = CH₃, R² = 4-CH₃C(═O)—Ph—)
Compound T2 (R¹ = CH₃, R² = Ph—)
Compound T3 (R¹ = CH₃, R² = Ph—CH(—OH)—)

To a solution of N—CBZ-Thr-OH(R¹═CH₃) in CH₂Cl₂ (Concentration=0.3M), 2,6-Lutidine was added (1.3 eq.), then tert-Butyldimethylsilyl trifluoromethanesulfonate (TBDMSOTf) (3 eq.), while stirring under argon at 0° C. The reaction was stirred for 4 hours and the temperature was let spontaneously rise to room temperature. The crude was washed twice with 5% aq. citric acid, and once with saturated NaCl. The combined organic layers were dried with Na₂SO₄, and the solvent evaporated under reduced pressure. The crude was purified by silica gel column chromatography using 5% Methanol/Dichloromethane.

To a solution of intermediate (17) and 3,5-diaminopiperidine(Boc)₂ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO₃ and once with saturated NaCl. The combined organic layers were dried over Na₂SO₄ and the solvent was removed under reduced pressure. The crude product 18 was purified by silica gel chromatography, using 2% (v/v) methanol (MeOH)/dichloromethane (DCM).

The pure compound (18) was dissolved in anhydrous methanol (0.1 M) and the solution was flushed with argon. Following slow addition of Pd on carbon catalyst (Pd/C, 10% by weight), the solution was purged twice with hydrogen gas, using a hydrogen balloon. The third balloon was left for the reaction to stir at room temperature for 16-24 hrs. The reaction mixture was filtered over a pad of celite and the solvent was removed under reduced pressure. The crude product was purified by silica gel column chromatography starting at 2% (v/v) MeOH/DCM and ending at 6% MeOH/DCM, with increments of 1%.

To a solution of intermediate 18 and 4-acetylbenzoic acid (1 eq.) in dichloromethane (0.05M), triethylamine (7 eq.) was added, followed by HATU (1.1 eq.) and HOAT (1.2 eq.), while stirring under argon at 0° C. for the synthesis of compound T1. To a solution of intermediate 18 and benzoic acid (1 eq.) in dichloromethane (0.05M), triethylamine (7 eq.) was added, followed by HATU (1.1 eq.) and HOAT (1.2 eq.), while stirring under argon at 0° C. for the synthesis of compound T2. To a solution of intermediate 18 and lactic acid (1 eq.) in dichloromethane (0.05M), triethylamine (7 eq.) was added, followed by HATU (1.1 eq.) and HOAT (1.2 eq.), while stirring under argon at 0° C. for the synthesis of compound T3. For each compound, the reaction mixture was stirred for 3.5 hours and the temperature was let equilibrate to room temperature. The reaction progress was monitored by TLC. Upon complete consumption of starting material, the reaction mixture was diluted with dichloromethane and washed once with 0.1 M HCl, once with saturated NaHCO₃ and once with saturated NaCl. The combined organic layers were dried over Na₂SO₄ and the solvent was removed under reduced pressure. The crude product was purified by silica gel chromatography, starting at 2% (v/v) MeOH/DCM and continuing at 3% MeOH/DCM.

To a solution of intermediate 19 in THF (Concentration=0.05M), a solution of tert-butylammonium fluoride (TBAF) was added (3 eq. of TBAF), while stirring under argon at 0° C. The reaction was stirred for 4 hours and the temperature was let equilibrate to room temperature. The reaction mixture was diluted with ethyl acetate, washed twice with H₂O and once with saturated NaCl. The combined organic layers were dried with Na₂SO₄, and the solvent evaporated under reduced pressure. The crude was purified by silica gel column chromatography using 7.5% Methanol/Dichloromethane.

The product of the previous coupling reaction was dissolved (0.02M) in a mixture of anhydrous methanol (2 parts) and 4M HCl/dioxane (1 part), while stirring under argon at 0° C. The reaction mixture was stirred for 3-5 hours and the temperature was let equilibrate to room temperature. The reaction mixture was diluted threefold with toluene and the solvent was removed under reduced pressure. The process of adding toluene and evaporating was repeated twice.

The crude compound (50 mg) was dissolved in deionized water (1 mL) and sonicated for ten minutes. The solution was filtered and centrifuged. The solution was injected multiple times (99 μL maximum) into a C18 semi preparative HPLC column. The elution was monitored by UV Vis, at λ=205 nm, λ=220 nm and λ=257 nm (elution gradient: 5-30% H₂O/ACN, 0.1% TFA, in 25 minutes). The peaks containing the product from the several injections were combined and the solvent was removed by lyophilization, yielding a white flaky solid. The compound was characterized by NMR and mass-spectrometry.

Example 10

Synthesis of Compound T4 and T5

The synthetic procedures to produce compounds T4 and T5 generally follow the procedures outlined in Example 7. In the synthesis of compound T4, 4-acetylbenzoic acid is replaced by lactic acid. In the synthesis of compound T5, 4-acetylbenzoic acid is replaced by 4-hydroxylbenzoic acid.

Example 11

Synthesis of Compound S6

To a solution of N—CBZ-Ser-OH(R₁═H) in CH₂Cl₂ (Concentration=0.3M), 2,6-Lutidine was added (1.3 eq.), then tert-Butyldimethylsilyl trifluoromethanesulfonate (TB-DMSOTf) (3 eq.), while stirring under argon at 0° C. The reaction was stirred for 4 hours and the temperature was let spontaneously rise to room temperature. The crude was washed twice with 5% aq. citric acid, and once with saturated NaCl. The combined organic layers were dried with $Na_2SO_4$, and the solvent evaporated under reduced pressure. The crude was purified by silica gel column chromatography using 5% Methanol/Dichloromethane.

To a solution of intermediate (17) and 3,5-diaminopiperidine(Boc)$_2$ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated $NaHCO_3$ and once with saturated NaCl. The combined organic layers were dried over $Na_2SO_4$ and the solvent was removed under reduced pressure. The crude product 18 was purified by silica gel chromatography, using 2% (v/v) methanol (MeOH)/dichloromethane (DCM).

The pure compound (18) is dissolved in anhydrous methanol (0.1 M) and the solution is flushed with argon. Following slow addition of Pd on carbon catalyst (Pd/C 10% by weight), the solution is purged twice with hydrogen gas, using a hydrogen balloon. The third balloon is left for the reaction to stir at room temperature for 24 hrs. The reaction mixture is then filtered over a pad of celite to remove the catalyst. To the methanol solution 4M HCl/dioxane were added (1 eq.), while stirring under argon at 0° C. The reaction mixture is stirred for 4 hours and the temperature is let equilibrate to room temperature. The reaction mixture is then diluted threefold with toluene and the solvent is removed under reduced pressure. The process of adding toluene and evaporating is repeated twice. Finally, the crude compound is dissolved in deionized water.

The crude compound (50 mg) is dissolved in deionized water (1 mL) and sonicated for ten minutes. The solution is filtered and centrifuged. The solution is injected multiple times (99 μL maximum) into a C18 semi preparative HPLC column. The elution is monitored by UV Vis, at $\lambda$=205 nm, $\lambda$=220 nm and $\lambda$=257 nm (elution gradient: 5-30% $H_2O$/ACN, 0.1% TFA, in 25 minutes). The peaks containing the product from the several injections were combined and the solvent is removed by lyophilization, yielding a white flaky solid. The compound is characterized by NMR and mass-spectrometry.

Example 12

Synthesis of Compound T6

To a solution of N—CBZ-Thr-OH($R^1$=$CH_3$) in $CH_2Cl_2$ (Concentration=0.3M), 2,6-Lutidine was added (1.3 eq.), then tert-Butyldimethylsilyl trifluoromethanesulfonate (TB-DMSOTf) (3 eq.), while stirring under argon at 0° C. The reaction was stirred for 4 hours and the temperature was let spontaneously rise to room temperature. The crude was washed twice with 5% aq. citric acid, and once with saturated NaCl. The combined organic layers were dried with $Na_2SO_4$, and the solvent evaporated under reduced pressure. The crude was purified by silica gel column chromatography using 5% Methanol/Dichloromethane.

To a solution of intermediate (17) and 3,5-diaminopiperidine(Boc)$_2$ (3) (1 eq.) in dichloromethane (0.1 M), triethylamine (7 eq.) was added, followed by HATU (1.1 eq.) and HOAT (1.2 eq.), while stirring under argon at 0° C. The reaction mixture was stirred for 5 hours and the temperature was let equilibrate to room temperature. The reaction progress was monitored by TLC. Upon complete consumption of starting material, the reaction mixture was diluted with dichloromethane and washed once with 0.1 M HCl, once with saturated $NaHCO_3$ and once with saturated NaCl. The combined organic layers were dried over $Na_2SO_4$ and the solvent was removed under reduced pressure. The crude product 18 was purified by silica gel chromatography, using 2% (v/v) methanol (MeOH)/dichloromethane (DCM).

The pure compound (18) is dissolved in anhydrous methanol (0.1 M) and the solution is flushed with argon. Following slow addition of Pd on carbon catalyst (Pd/C 10% by weight), the solution is purged twice with hydrogen gas, using a hydrogen balloon. The third balloon is left for the reaction to stir at room temperature for 24 hrs. The reaction mixture is then filtered over a pad of celite to remove the catalyst. To the methanol solution 4M HCl/dioxane were added (1 eq.), while stirring under argon at 0° C. The reaction mixture is stirred for 4 hours and the temperature is let equilibrate to room temperature. The reaction mixture is then diluted threefold with toluene and the solvent is removed under reduced pressure. The process of adding toluene and evaporating is repeated twice. Finally, the crude compound is dissolved in deionized water.

The crude compound (50 mg) is dissolved in deionized water (1 mL) and sonicated for ten minutes. The solution is filtered and centrifuged. The solution is injected multiple times (99 μL maximum) into a C18 semi preparative HPLC column. The elution is monitored by UV Vis, at $\lambda$=205 nm, $\lambda$=220 nm and $\lambda$=257 nm (elution gradient: 5-30% $H_2O$/ACN, 0.1% TFA, in 25 minutes). The peaks containing the product from the several injections were combined and the solvent is removed by lyophilization, yielding a white flaky solid. The compound is characterized by NMR and mass-spectrometry.

What is claimed is:
1. A compound of Formula (I) or a pharmaceutically acceptable salt thereof:

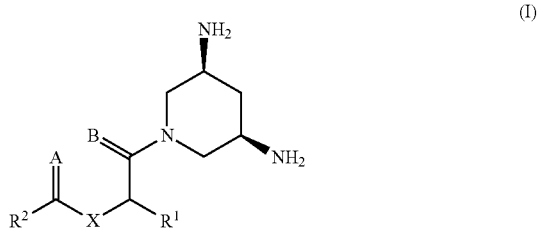

wherein:
X is NH, O, S, or $(CH_2)_{n1}$, wherein $n_1$ is 1 to 6;
A is O or S;
B is O or S;
each $R^1$ and $R^2$, independently, is —$CONH_2$, or a substituted or unsubstituted —$C_{1-6}$ alkyl, a substituted or unsubstituted aryl, a substituted or unsubstituted heteroaryl, a substituted or unsubstituted —$(CH_2)_n$ aryl, a substituted or unsubstituted —$(CH_2)_n$ heteroaryl, a substituted or unsubstituted —$(CH_2)_n$ heterocycloalkyl, a substituted or unsubstituted —(CH=CH)$_n$ aryl, a substituted or unsubstituted —(CH=CH)$_n$ heteroaryl, a substituted or unsubstituted —$C_{2-6}$ alkenyl-aryl, a substituted or unsubstituted —C$_{2-6}$ alkenyl-heteroaryl, a substituted or unsubstituted —(C≡C)$_n$ aryl, a substituted or unsubstituted —(C≡C)$_n$ heteroaryl, a substituted or unsubstituted —NR$^3$—C$_{1-6}$ alkyl, a substituted or unsubstituted —NR$^3$-aryl, a substituted or unsubstituted —NR$^3$-heteroaryl, a substituted or unsubstituted —NR$^3$-cycloalkyl, a substituted or unsubstituted —NR$^3$-heterocycloalkyl, a substituted or unsubstituted —NHNH—C$_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—C$_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, —S(C$_{1-6}$) alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C═O)(C$_{1-6}$) alkyl, a substituted or unsubstituted —(C═O) aryl, a substituted or unsubstituted —(C═O) heterocycloalkyl, n being an integer from 1 to 4; and R$^3$ is —H or a substituted or unsubstituted alkyl, aryl, heteroaryl, cycloalkyl, or heterocycloalkyl.

2. The compound of claim 1, wherein X is NH.

3. The compound of claim 1, wherein X is CH$_2$.

4. A compound of Formula (II) or a pharmaceutically acceptable salt thereof:

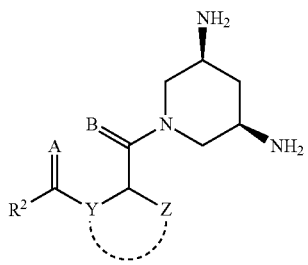

II wherein:
A is O or S;
B is O or S;
Y is N or CH, or —(CH$_2$)$_{n2}$CH—, wherein n$_2$ is from 1 to 6;
Z is a lower alkylene group or a lower heteroalkylene group such that Z and Y together with the C atom between them form a 4-, 5-, or 6-membered substituted or unsubstituted cycloalkyl or heterocycloalkyl;
each R$^2$ is —CONH$_2$, or a substituted or unsubstituted —C$_{1-6}$ alkyl, a substituted or unsubstituted aryl, a substituted or unsubstituted heteroaryl, a substituted or unsubstituted —(CH$_2$)$_n$ aryl, a substituted or unsubstituted —(CH$_2$)$_n$ heteroaryl, a substituted or unsubstituted —(CH$_2$)$_n$ heterocycloalkyl, a substituted or unsubstituted —(CH═CH)$_n$ aryl, a substituted or unsubstituted —(CH═CH)$_n$ heteroaryl, a substituted or unsubstituted —C$_{2-6}$ alkenyl-aryl, a substituted or unsubstituted —C$_{2-6}$ alkenyl-heteroaryl, a substituted or unsubstituted —(C≡C)$_n$ aryl, a substituted or unsubstituted —(C≡C)$_n$ heteroaryl, a substituted or unsubstituted —NR$^3$—C$_{1-6}$ alkyl, a substituted or unsubstituted —NR$^3$-aryl, a substituted or unsubstituted —NR$^3$-heteroaryl, a substituted or unsubstituted —NR$^3$-cycloalkyl, a substituted or unsubstituted —NR$^3$-heterocycloalkyl, a substituted or unsubstituted —NHNH—C$_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—C$_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, a substituted or unsubstituted —S(C$_{1-6}$) alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C═O)(C$_{1-6}$) alkyl, a substituted or unsubstituted —(C═O) aryl, a substituted or unsubstituted —(C═O) heterocycloalkyl, n being an integer from 1 to 4; and R$^3$ is —H or a substituted or unsubstituted alkyl, aryl, heteroaryl, cycloalkyl, or heterocycloalkyl.

5. A compound of claim 1, where the compound is:

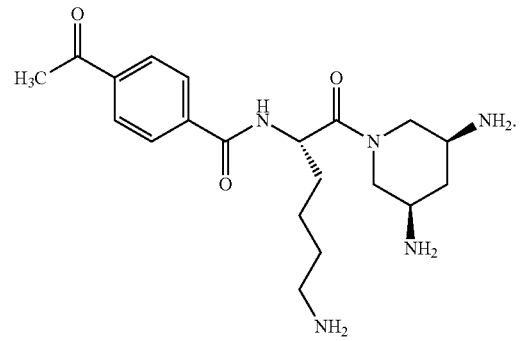

6. A compound of claim 1, wherein R$^1$ is:
—(CH$_2$)$_{n3}$—NH$_2$, where n$_3$ is 1 to 6

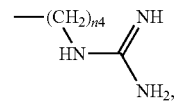

where n$_4$ is 1 to 5

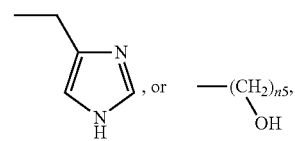

where n$_5$ is 1 to 3, and $R^2$ is:
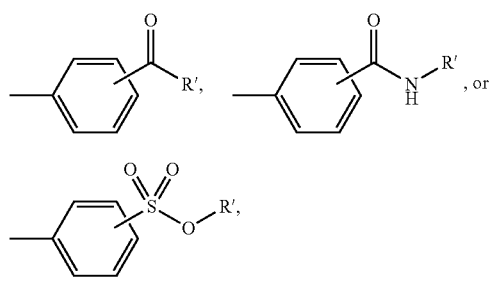
wherein R' is an alkyl, aryl, heteroaryl, heterycycloalkyl, alkenyl-aryl, cycloalkyl, or alkenyl-heteroaryl.
7. A compound of claim 1, wherein $R^1$ is:
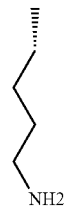
and $R^2$ is
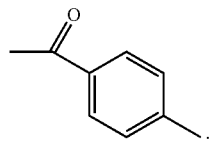
8. A compound of claim 1, wherein $R^1$ is:
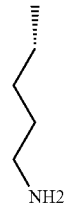
and $R^2$ is
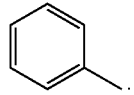
9. A compound of claim 1, wherein $R^1$ is:
and $R^2$ is
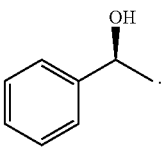
10. A compound of claim 1, wherein $R^1$ is:
and $R^2$ is
11. A compound of claim 1, wherein $R^1$ is:
and $R^2$ is
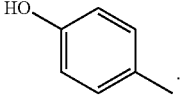

12. A compound of claim 1, wherein $R^1$ is:
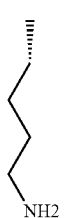
and $R^2$ is H.
13. A compound of claim 1, wherein $R^1$ is:
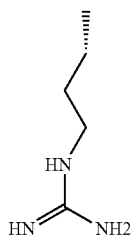
and $R^2$ is
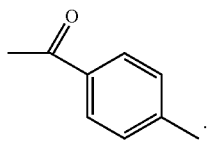
14. A compound of claim 1, wherein $R^1$ is:
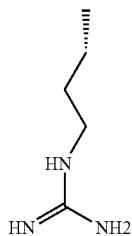
and $R^2$ is
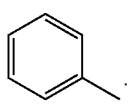
15. A compound of claim 1, wherein $R^1$ is:
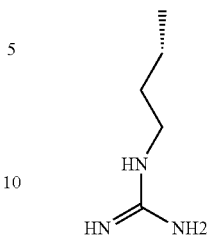
and $R^2$ is
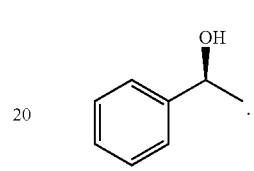
16. A compound of claim 1, wherein $R^1$ is:
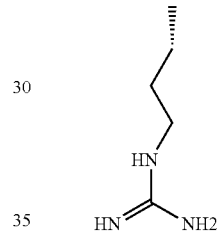
and $R^2$ is
17. A compound of claim 1, wherein $R^1$ is:
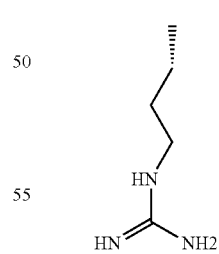
and $R^2$ is
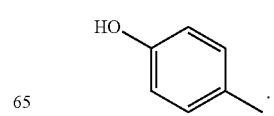

18. A compound of claim 1, wherein $R^1$ is:

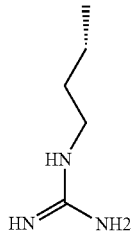

and $R^2$ is H.

19. A compound of claim 1, wherein $R^1$ is:

and $R^2$ is

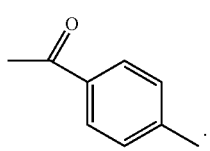

20. A compound of claim 1, wherein $R^1$ is:

and $R^2$ is

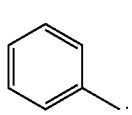

21. A compound of claim 1, wherein $R^1$ is:

and $R^2$ is

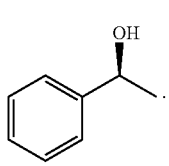

22. A compound of claim 1, wherein $R^1$ is:

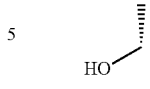

and $R^2$ is

23. A compound of claim 1, wherein $R^1$ is:

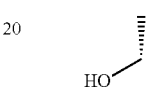

and $R^2$ is

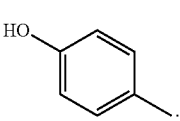

24. A compound of claim 1, wherein $R^1$ is:

and $R^2$ is H.

25. A compound of claim 1, wherein $R^1$ is:

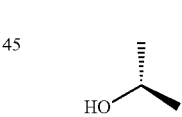

and $R^2$ is

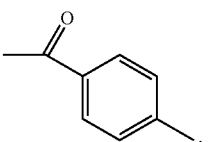

26. A compound of claim 1, wherein $R^1$ is:

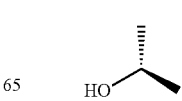

and R² is

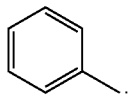

27. A compound of claim 1, wherein R¹ is:

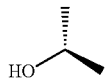

and R² is

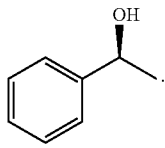

28. A compound of claim 1, wherein R¹ is:

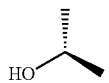

and R² is

29. A compound of claim 1, wherein R¹ is:

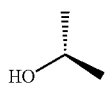

and R² is

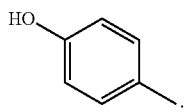

30. A compound of claim 1, wherein R¹ is:

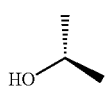

and R² is H.

31. A pharmaceutical composition comprising a pharmaceutically acceptable carrier and an effective amount of a compound of Formula (I) or a pharmaceutically acceptable salt thereof:

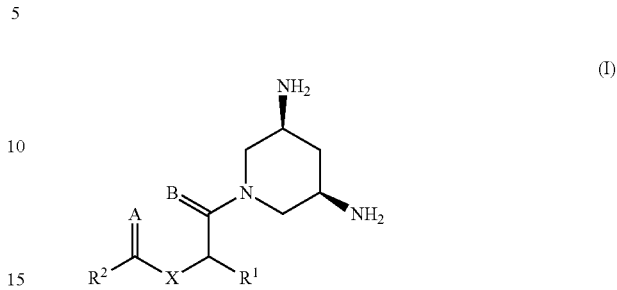

(I)

wherein:

X is NH, O, S, or $(CH_2)_{n1}$, wherein $n_1$ is 1 to 6;

A is O or S;

B is O or S;

each R¹ and R², independently, is —CONH$_2$, or a substituted or unsubstituted —C$_{1-6}$ alkyl, a substituted or unsubstituted aryl, a substituted or unsubstituted heteroaryl, a substituted or unsubstituted —(CH$_2$)$_n$ aryl, a substituted or unsubstituted —(CH$_2$)$_n$ heteroaryl, a substituted or unsubstituted —(CH$_2$)$_n$ heterocycloalkyl, a substituted or unsubstituted —(CH=CH)$_n$ aryl, a substituted or unsubstituted —(CH=CH)$_n$ heteroaryl, a substituted or unsubstituted —C$_{2-6}$ alkenyl-aryl, a substituted or unsubstituted —C$_{2-6}$ alkenyl-heteroaryl, a substituted or unsubstituted —(C≡C)$_n$ aryl, a substituted or unsubstituted —(C≡C)$_n$ heteroaryl, a substituted or unsubstituted —NR³—C$_{1-6}$ alkyl, a substituted or unsubstituted —NR³-aryl, a substituted or unsubstituted —NR³-heteroaryl, a substituted or unsubstituted —NR³-cycloalkyl, a substituted or unsubstituted —NR³-heterocycloalkyl, a substituted or unsubstituted —NHNH—C$_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—C$_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, —S(C$_{1-6}$) alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C=O)(C$_{1-6}$) alkyl, a substituted or unsubstituted —(C=O) aryl, a substituted or unsubstituted —(C=O) heterocycloalkyl, n being an integer from 1 to 4; and R³ is —H or a substituted or unsubstituted alkyl, aryl, heteroaryl, cycloalkyl, or heterocycloalkyl.

32. The pharmaceutical composition of claim 31, wherein said pharmaceutical composition is a pill comprising an effective amount of said compound of Formula (I).

33. An injection device comprising a compound of Formula (I).

34. The injection device of claim 33, wherein said injection device is a syringe.

35. A pharmaceutical composition comprising a pharmaceutically acceptable carrier and an effective amount of a compound of Formula (II) or a pharmaceutically acceptable salt thereof:

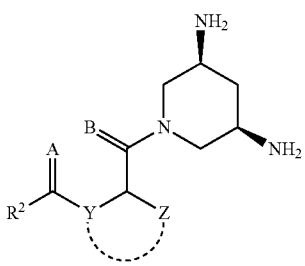

II wherein:
A is O or S;
B is O or S;
Y is N or CH, or —(CH$_2$)$_{n_2}$CH—, wherein n$_2$ is from 1 to 6;
Z is a lower alkylene group or a lower heteroalkylene group such that Z and Y together with the C atom between them form a 4-, 5-, or 6-membered substituted or unsubstituted cycloalkyl or heterocycloalkyl;
each R$^2$ is —CONH$_2$, or a substituted or unsubstituted —C$_{1-6}$ alkyl, a substituted or unsubstituted aryl, a substituted or unsubstituted heteroaryl, a substituted or unsubstituted —(CH$_2$)$_n$ aryl, a substituted or unsubstituted —(CH$_2$)$_n$ heteroaryl, a substituted or unsubstituted —(CH$_2$)$_n$ heterocycloalkyl, a substituted or unsubstituted —(CH=CH)$_n$ aryl, a substituted or unsubstituted —(CH=CH)$_n$ heteroaryl, a substituted or unsubstituted —C$_{2-6}$ alkenyl-aryl, a substituted or unsubstituted —C$_{2-6}$ alkenyl-heteroaryl, a substituted or unsubstituted —(C≡C)$_n$ aryl, a substituted or unsubstituted —(C≡C)$_n$ heteroaryl, a substituted or unsubstituted —NR$^3$—C$_{1-6}$ alkyl, a substituted or unsubstituted —NR$^3$-aryl, a substituted or unsubstituted —NR$^3$-heteroaryl, a substituted or unsubstituted —NR$^3$-cycloalkyl, a substituted or unsubstituted —NR$^3$-heterocycloalkyl, a substituted or unsubstituted —NHNH—C$_{1-6}$ alkyl, a substituted or unsubstituted —NHNH-aryl, a substituted or unsubstituted —NHNH-heteroaryl, a substituted or unsubstituted —NHNH-cycloalkyl, a substituted or unsubstituted —NHNH-heterocycloalkyl, a substituted or unsubstituted —O—C$_{1-6}$ alkyl, a substituted or unsubstituted —O-aryl, a substituted or unsubstituted —O-heteroaryl, a substituted or unsubstituted —O-cycloalkyl, a substituted or unsubstituted —O-heterocycloalkyl, a substituted or unsubstituted —S(C$_{1-6}$) alkyl, a substituted or unsubstituted —S-aryl, a substituted or unsubstituted —S-heteroaryl, a substituted or unsubstituted —S-cycloalkyl, a substituted or unsubstituted —S-heterocycloalkyl, a substituted or unsubstituted —(C=O)(C$_{1-6}$) alkyl, a substituted or unsubstituted —(C=O) aryl, a substituted or unsubstituted —(C=O) heterocycloalkyl, n being an integer from 1 to 4; and
R$^3$ is —H or a substituted or unsubstituted alkyl, aryl, heteroaryl, cycloalkyl, or heterocycloalkyl.

36. The pharmaceutical composition of claim 31, wherein said pharmaceutical composition is a pill comprising an effective amount of said compound of Formula (II).

37. An injection device comprising a compound of Formula (II).

38. The injection device of claim 33, wherein said injection device is a syringe.

* * * * *